US010722346B2

(12) United States Patent
Valle et al.

(10) Patent No.: US 10,722,346 B2
(45) Date of Patent: Jul. 28, 2020

(54) INTRAOCULAR LENS INJECTOR ASSEMBLY HAVING SHUTTLE ASSEMBLY RETAINING INTRAOCULAR LENS IN STORAGE VIAL AND OPERABLY PRESENTING INTRAOCULAR LENS IN INJECTOR ASSEMBLY

(71) Applicant: Bausch & Lomb Incorporated, Rochester, NY (US)

(72) Inventors: Moises A. Valle, Tustin, CA (US); Madhu S. Ayyagari, Sr., Rancho Santa Margarita, CA (US); Sushant P. Muchhala, Aliso Viejo, CA (US); Sanjeev Bakshi, Trabuco Canyon, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 198 days.

(21) Appl. No.: 15/708,873

(22) Filed: Sep. 19, 2017

(65) Prior Publication Data
US 2019/0083237 A1 Mar. 21, 2019

(51) Int. Cl.
*A61F 2/16* (2006.01)

(52) U.S. Cl.
CPC .......... *A61F 2/1664* (2013.01); *A61F 2/1667* (2013.01); *A61F 2/1678* (2013.01); *A61F 2/1691* (2013.01)

(58) Field of Classification Search
CPC ...... A61F 2/1678; A61F 2/1662; A61F 2/167; A61F 2/1691; A61F 9/0017; A61F 2/1664; A61F 2/1667; A61F 9/009; A61F 9/013; A61F 9/007; A61F 9/00812; A61F 9/00827; A61F 2009/00872; A61F 2009/0052; A61F 2009/00865; A61F 2009/0087
See application file for complete search history.

(56) References Cited

U.S. PATENT DOCUMENTS

| 4,834,094 A | 5/1989 | Patton et al. |
| 5,425,734 A | 6/1995 | Blake |
| 5,468,246 A | 11/1995 | Blake |

(Continued)

FOREIGN PATENT DOCUMENTS

| EP | 0363213 A2 | 4/1990 |
| EP | 0785760 B1 | 12/2000 |

(Continued)

*Primary Examiner* — Darwin P Erezo
*Assistant Examiner* — Mohamed G Gabr
(74) *Attorney, Agent, or Firm* — Brian B. Shaw, Esq.; Timothy W. Menasco, Esq.; Harter Secrest & Emery LLP

(57) ABSTRACT

A shuttle, vial and injector are provided for storing and presenting an IOL to a patient. The shuttle includes operably engaged shuttle plates having a set of confronting surfaces that flex about a flexure interface between a storage configuration, with at least an optic of an IOL in a nominal state and a loading configuration, with at least an optic of an IOL in a deformed state. The vial engages the shuttle and maintains the shuttle in the storage configuration. The injector receives the shuttle from the vial and includes surfaces for flexing the portions of the shuttle plates to the loading configuration upon engagement with the injector, wherein the shuttle plates impart a predetermined curvature to at least a portion of the IOL.

15 Claims, 16 Drawing Sheets

(56) References Cited

U.S. PATENT DOCUMENTS

| | | | |
|---|---|---|---|
| 5,494,484 A | 2/1996 | Feingold | |
| 5,499,987 A | 3/1996 | Feingold | |
| 5,582,614 A | 12/1996 | Feingold | |
| 5,616,148 A | 4/1997 | Eagles et al. | |
| 5,620,450 A | 4/1997 | Eagles et al. | |
| 5,728,102 A | 3/1998 | Feingold et al. | |
| 5,800,442 A | 9/1998 | Wolf et al. | |
| 5,873,879 A | 2/1999 | Figueroa et al. | |
| 5,876,406 A | 3/1999 | Wolf et al. | |
| 5,928,245 A | 7/1999 | Wolf et al. | |
| 5,947,974 A * | 9/1999 | Brady | A61F 2/1691 606/1 |
| 6,001,107 A | 12/1999 | Feingold | |
| 6,142,999 A | 11/2000 | Brady et al. | |
| RE37,387 E | 9/2001 | Brady et al. | |
| 6,312,433 B1 | 11/2001 | Butts et al. | |
| 6,336,932 B1 | 1/2002 | Figueroa et al. | |
| 6,387,101 B1 | 5/2002 | Butts et al. | |
| 6,503,275 B1 | 1/2003 | Cumming | |
| 6,554,839 B2 | 4/2003 | Brady | |
| 6,712,848 B1 | 3/2004 | Wolf et al. | |
| 6,733,507 B2 | 5/2004 | McNicholas et al. | |
| 7,033,366 B2 | 4/2006 | Brady | |
| 7,037,328 B2 | 5/2006 | Vincent | |
| 7,276,071 B2 | 10/2007 | Lin et al. | |
| 7,429,263 B2 | 9/2008 | Vaquero et al. | |
| 7,901,414 B2 | 3/2011 | Tourrette et al. | |
| 8,273,122 B2 | 9/2012 | Anderson | |
| 8,308,736 B2 | 11/2012 | Boukhny et al. | |
| 8,470,030 B2 | 6/2013 | Meunier et al. | |
| 8,470,031 B2 | 6/2013 | Pankin et al. | |
| 8,475,528 B2 | 7/2013 | Ichinohe et al. | |
| 8,858,625 B2 | 10/2014 | Putallaz et al. | |
| 9,101,465 B2 | 8/2015 | Berner et al. | |
| 9,277,989 B2 | 3/2016 | Vaquero et al. | |
| 9,301,833 B2 | 4/2016 | Gulati et al. | |
| 9,504,561 B2 | 11/2016 | Wu | |
| 2004/0127911 A1 | 7/2004 | Figueroa et al. | |
| 2005/0283162 A1 | 12/2005 | Stratas | |
| 2005/0283163 A1 | 12/2005 | Portney et al. | |
| 2006/0142780 A1 | 6/2006 | Pynson et al. | |
| 2006/0142781 A1 | 6/2006 | Pynson et al. | |
| 2006/0167466 A1 | 7/2006 | Dusek | |
| 2007/0050023 A1 | 3/2007 | Bessiere et al. | |
| 2007/0055370 A1 | 3/2007 | Sorochkin et al. | |
| 2007/0060925 A1 | 3/2007 | Pynson | |
| 2008/0119864 A1 | 5/2008 | Deinzer et al. | |
| 2009/0018548 A1 | 1/2009 | Charles | |
| 2009/0125034 A1 | 5/2009 | Pynson | |
| 2010/0228261 A1 | 9/2010 | Feingold et al. | |
| 2011/0213380 A1 | 9/2011 | Han | |
| 2011/0245840 A1 | 10/2011 | Seyboth et al. | |
| 2012/0016374 A1 * | 1/2012 | Han | A61F 2/1678 606/107 |
| 2012/0289969 A1 | 11/2012 | Seyboth et al. | |
| 2013/0041382 A1 | 2/2013 | Ben Nun | |
| 2014/0066946 A1 | 3/2014 | Aguilera et al. | |
| 2014/0074107 A1 * | 3/2014 | Biddle | A61F 2/167 606/107 |
| 2014/0378987 A1 | 12/2014 | Putallaz et al. | |
| 2015/0045805 A1 | 2/2015 | Kontur et al. | |
| 2016/0270907 A1 | 9/2016 | Attinger | |
| 2016/0287382 A1 | 10/2016 | Hangya et al. | |

FOREIGN PATENT DOCUMENTS

| | | | |
|---|---|---|---|
| EP | 0723429 B1 | 4/2002 | |
| EP | 0722292 B1 | 7/2003 | |
| EP | 0743840 B1 | 7/2003 | |
| EP | 0901343 B1 | 8/2003 | |
| EP | 0727966 B1 | 9/2003 | |
| EP | 1023880 B1 | 10/2003 | |
| EP | 1011561 B1 | 9/2004 | |
| EP | 1037573 B1 | 9/2004 | |
| EP | 1491163 A2 | 12/2004 | |
| EP | 1367964 B1 | 7/2007 | |
| EP | 1795154 B1 | 10/2008 | |
| EP | 1718247 B1 | 4/2009 | |
| EP | 1659991 B1 | 5/2009 | |
| EP | 1453440 B1 | 9/2009 | |
| EP | 2111820 A1 | 10/2009 | |
| EP | 1905386 B1 | 6/2011 | |
| EP | 2332494 A1 | 6/2011 | |
| EP | 2062552 B1 | 7/2011 | |
| EP | 1833422 B1 | 11/2011 | |
| EP | 1833423 B1 | 4/2014 | |
| EP | 2408398 B1 | 6/2014 | |
| EP | 2873391 A1 | 5/2015 | |
| EP | 2838471 B1 | 3/2016 | |
| EP | 1838243 B1 | 4/2016 | |
| EP | 2334259 B1 | 5/2016 | |
| EP | 2925260 B1 | 10/2016 | |
| EP | 2355747 B1 | 11/2016 | |
| JP | 2156943 A2 | 6/1990 | |
| JP | 3556225 B2 | 8/2004 | |
| JP | 3664444 B2 | 6/2005 | |
| JP | 3687973 B2 | 8/2005 | |
| JP | 3704154 B2 | 10/2005 | |
| JP | 3937181 B2 | 6/2007 | |
| JP | 4031617 B2 | 1/2008 | |
| JP | 4035169 B2 | 1/2008 | |
| JP | 4077727 B2 | 4/2008 | |
| JP | 2009213904 A | 9/2009 | |
| JP | 4353805 B2 | 10/2009 | |
| JP | 4460579 B2 | 5/2010 | |
| JP | 4520255 B2 | 8/2010 | |
| JP | 4767671 B2 | 9/2011 | |
| JP | 4955573 B2 | 6/2012 | |
| JP | 2013523269 A | 6/2013 | |
| JP | 5450783 B2 | 3/2014 | |
| JP | 5497771 B2 | 5/2014 | |
| JP | 2015514517 A | 5/2015 | |
| JP | 2015527168 A | 9/2015 | |
| JP | 5852582 B2 | 2/2016 | |
| JP | 2016508821 A | 3/2016 | |
| WO | 1994007436 A1 | 4/1994 | |
| WO | 1995013022 A1 | 5/1995 | |
| WO | 1995013766 A1 | 5/1995 | |
| WO | 9522287 A1 | 8/1995 | |
| WO | 1996011649 A1 | 4/1996 | |
| WO | 1996015743 A1 | 5/1996 | |
| WO | 1996028121 A1 | 9/1996 | |
| WO | 1998005281 A1 | 2/1998 | |
| WO | 1998020819 A1 | 5/1998 | |
| WO | 1999029267 A1 | 6/1999 | |
| WO | 2001028475 A1 | 4/2001 | |
| WO | 2001064147 A1 | 9/2001 | |
| WO | 02071982 A1 | 9/2002 | |
| WO | 2002074202 A1 | 9/2002 | |
| WO | 2003049645 A2 | 6/2003 | |
| WO | 2005023154 A2 | 3/2005 | |
| WO | 2005025459 A1 | 3/2005 | |
| WO | 2005030097 A1 | 4/2005 | |
| WO | 2005082285 A1 | 9/2005 | |
| WO | 2005117781 A2 | 12/2005 | |
| WO | 2006030082 A1 | 3/2006 | |
| WO | 2006070219 A1 | 7/2006 | |
| WO | 2006071561 A1 | 7/2006 | |
| WO | 2007027499 A2 | 3/2007 | |
| WO | 2008040446 A2 | 4/2008 | |
| WO | 2008087226 A1 | 7/2008 | |
| WO | 2008098384 A2 | 8/2008 | |
| WO | 2009012017 A1 | 1/2009 | |
| WO | 2010008850 A1 | 1/2010 | |
| WO | 2010028873 A1 | 3/2010 | |
| WO | 2010032993 A1 | 3/2010 | |
| WO | 2010044974 A1 | 4/2010 | |
| WO | 2010105678 A1 | 9/2010 | |
| WO | 2011069907 A1 | 6/2011 | |
| WO | 2011123345 A2 | 10/2011 | |
| WO | 2011138790 A1 | 11/2011 | |
| WO | 2013038021 A1 | 3/2013 | |
| WO | 2013159045 A1 | 10/2013 | |

(56) References Cited

FOREIGN PATENT DOCUMENTS

| | | |
|---|---|---|
| WO | 2014039326 A1 | 3/2014 |
| WO | 2014039353 A1 | 3/2014 |
| WO | 2014074382 A2 | 8/2014 |
| WO | 2014137535 A1 | 9/2014 |
| WO | 2014207538 A2 | 12/2014 |
| WO | 2015070994 A1 | 5/2015 |
| WO | 2015075488 A1 | 5/2015 |
| WO | 2015075489 A2 | 5/2015 |
| WO | 2015112144 A1 | 7/2015 |
| WO | 2015193046 A1 | 12/2015 |

* cited by examiner

US 10,722,346 B2

INTRAOCULAR LENS INJECTOR ASSEMBLY HAVING SHUTTLE ASSEMBLY RETAINING INTRAOCULAR LENS IN STORAGE VIAL AND OPERABLY PRESENTING INTRAOCULAR LENS IN INJECTOR ASSEMBLY

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

Field of the Invention

The present disclosure relates to storing and presenting an intraocular lens (IOL) to a patient, and particularly to a kit having a shuttle, a vial and an injector, and more particularly to a shuttle that is moveable between an engaged IOL retaining storage configuration and an engaged IOL retaining loading configuration, wherein the vial interacts with the shuttle to dispose the shuttle in the storage configuration in which the IOL is retained in a nominal state and the injector interacts with the shuttle to dispose the shuttle in the loading configuration, in which at least a portion of the IOL retained in the shuttle is preferentially biased or deformed.

Description of Related Art

Intraocular lenses (also referred to herein as IOLs or simply as lenses) are artificial lenses used to replace natural crystalline lenses of eyes when the natural lenses are diseased or otherwise impaired. Under some circumstances a natural lens may remain in an eye together with an implanted IOL. IOLs may be placed in either the posterior chamber or the anterior chamber of an eye.

IOLs come in a variety of structures and materials. Various instruments and methods for implanting such IOLs in an eye are known. Typically, an incision is made in a cornea and an IOL is inserted into the eye through the incision. In one technique, a surgeon uses surgical forceps to grasp the IOL and insert it through the incision into the eye. While this technique is still practiced today, more and more surgeons are using IOL injectors which can offer advantages such as affording a surgeon more control when inserting an IOL into an eye and permitting insertion of IOLs through smaller incisions. Smaller incision sizes (e.g., less than about 3 mm) are preferred over larger incisions (e.g., about 3.2 to 5+ mm) since smaller incisions have been associated with to reduced post-surgical healing time and reduced complications such as induced astigmatism.

In order for an IOL to fit through a smaller incision, the IOL is typically folded and/or compressed prior to entering an eye where it will assume its original unfolded/uncompressed shape. Since IOLs are very small and delicate articles of manufacture, great care must be taken in their handling, both as they are loaded into an injector and as they are injected into the eye.

It is important that an IOL be expelled from the tip of the IOL injector and into the eye in an undamaged condition and in a predictable orientation. Should an IOL be damaged or expelled from the injector in an incorrect orientation, a surgeon must remove or further manipulate the IOL in the eye, possibly resulting in trauma to the surrounding tissues of the eye. To achieve proper delivery of an IOL, consistent loading of the IOL into the injector with a minimum opportunity for damaging the IOL is desirable.

Various IOL injectors and other devices have been proposed which attempt to address issues related to loading and presenting the IOL to the patient, yet there remains a need for a shuttle, vial and injector assembly which eliminates the need for operator handling of the IOL and thereby reduces the likelihood of damage to the IOL prior to presentation to a patient.

BRIEF SUMMARY OF THE INVENTION

The present disclosure provides a shuttle for retaining an IOL having an optic, the shuttle having a first shuttle plate and a separate second shuttle plate operably coupled and then configurable between a coupled storage configuration and a coupled loading configuration, the first and the second shuttle plates in each of the coupled storage configuration and the coupled loading configurations defining an IOL chamber extending along a longitudinal axis, the IOL chamber axially bounded by a proximal port and a distal port, wherein each of the proximal port and the distal port in each of the coupled storage configuration and the coupled loading configurations has a major dimension transverse to the longitudinal axis, the major dimension being smaller than a diameter of the optic.

The present disclosure further provides a shuttle for retaining an IOL having an optic, the shuttle including a first shuttle plate and a separate second shuttle plate configured to operably engage the first shuttle plate, such that the operably engaged first and second shuttle plates are configured to be disposed between an engaged storage configuration and an engaged loading configuration; wherein the operably engaged first and second shuttle plates define a shuttle having (i) a shuttle lumen extending along a longitudinal axis, the shuttle lumen having an IOL chamber sized to retain an optic of an IOL, (ii) a storage set of confronting surfaces, (iii) a loading set of confronting surfaces and (iv) a flexure interface intermediate the storage set of confronting surfaces and the loading set of confronting surfaces, wherein the operably engaged first and second shuttle plates contact the storage set of confronting surfaces in each of the engaged storage configuration and the engaged loading configuration, and the loading set of confronting surfaces flex from being spaced apart in the engaged storage configuration of the operably engaged first and second shuttle plates to abutting in the engaged loading configuration of the operably engaged first and second shuttle plates.

Also disclosed is a method of disposing an IOL having an optic within a shuttle, the method including the steps of capturing an IOL while located on a fixture within an IOL chamber defined by an engaged first shuttle plate and second shuttle plate, the engaged first shuttle plate and a second shuttle plate defining a shuttle; and withdrawing the fixture from the IOL through a port in the IOL chamber to retain the IOL within the IOL chamber defined by the engaged first shuttle plate and second shuttle plate.

BRIEF DESCRIPTION OF THE SEVERAL VIEWS OF THE DRAWING(S)

DETAILED DESCRIPTION OF THE INVENTION

Figure 1:
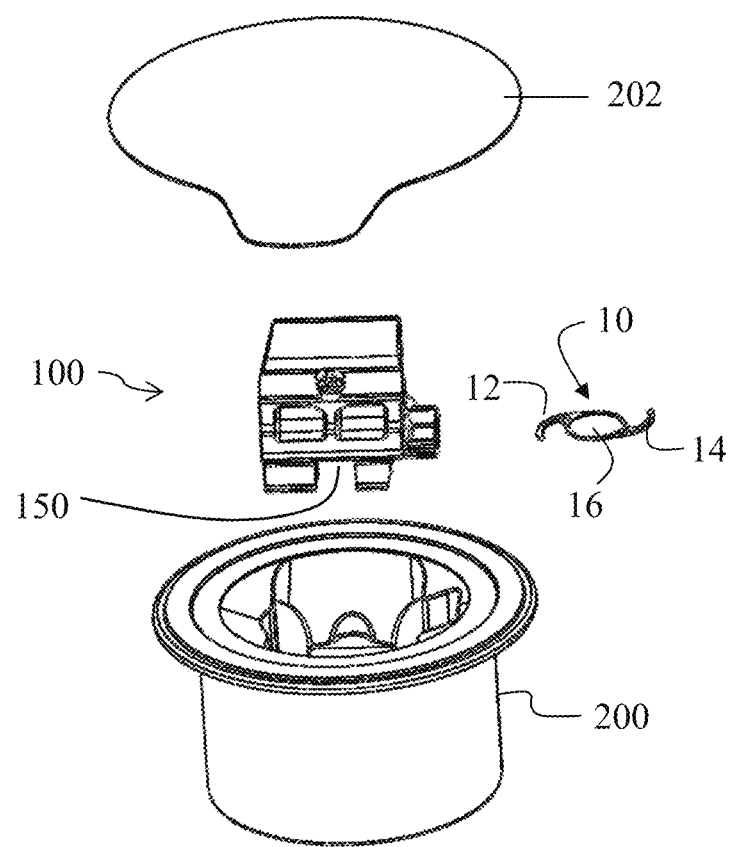
FIG. 1 is an exploded view of a shuttle, vial, a lid and an IOl, wherein the shuttle retains the IOL and the vial and lid retain the shuttle.

Generally, the present disclosure provides for a kit having a shuttle 100, a vial 200, and an injector 300, wherein the shuttle retains and stores an IOL 10, the vial retains the shuttle and the injector injects the IOL along a longitudinal axis into an eye of a patient.

As used herein, an IOL 10 is an artificial lens used to replace the natural crystalline lens of the eye when the natural lens has cataracts or is otherwise diseased. IOLs 10 are also sometimes implanted into an eye to correct refractive errors of the eye in which case the natural lens may remain in the eye together with the implanted IOL. The IOL 10 may be placed in either the posterior chamber or anterior chamber of the eye. IOLs 10 come in a variety of structures and materials. Some common IOL 10 styles include the so-called open-looped haptics which include the three-piece type having an optic and two haptics 12, 14 attached to and extending from an optic 16; the one-piece type wherein the optic and haptics are integrally formed (e.g., by machining the optic and haptics together from a single block of material); and also the closed looped haptic IOLs. A further style of IOL is called the plate haptic type wherein the haptics are configured as a flat plate extending from opposite sides of the optic. The IOL 10 may be made from a variety of materials or combination of materials such as, but not limited to PMMA, silicone, hydrogels and silicone hydrogels.

It is also understood that the IOL 10 structure shown and described herein is for discussion purposes only, and that the present invention is not to be limited by the particular structure of the IOL. The present system may be easily adapted to IOLs 10 of any structure and type (e.g., IOLs with plate, open or closed loop haptics, anterior chamber IOLs, posterior chamber IOLs, accommodating IOLs (including single and double lens types), etc.). The IOL 10 has a nominal state in the absence of external forces (other than gravity). That is, the nominal state is the formation the IOL assumes upon the removal of deforming forces.

Vial

Referring to FIG. 1, the vial 200 is sized to retain the shuttle 100, wherein the shuttle retains the IOL 10. The vial 200 can include a lid 202 for sealing the vial from an ambient environment. The vial 200 is sized to retain the shuttle 100 and IOL 10 along with a volume of sterile or sterilizing solution (not shown). Typically, the sterile solution is retained in the sealed vial 200 with the shuttle 100 and the IOL 10 to maintain the IOL in a sterile, liquid environment until intended use.

Figure 2:
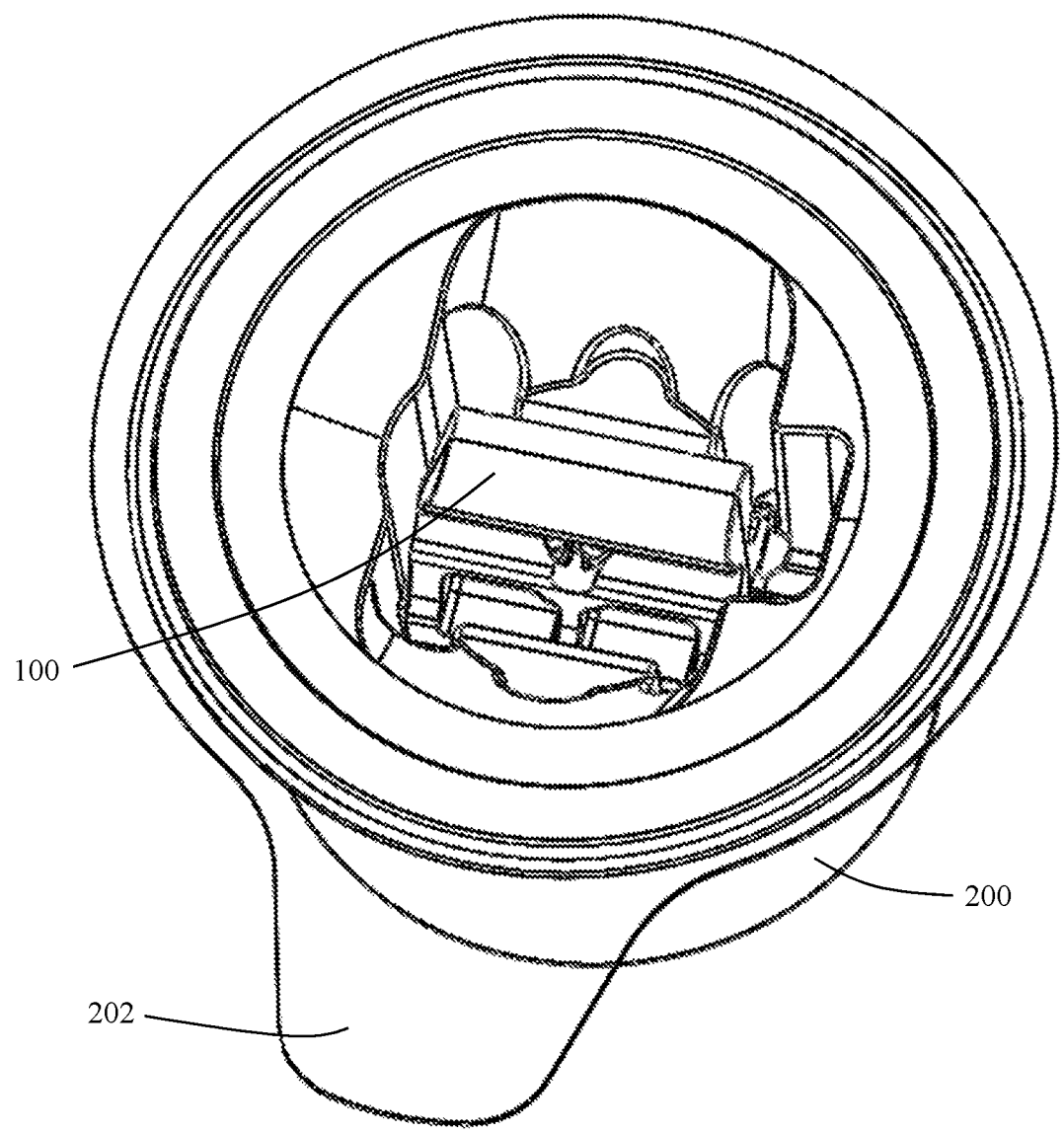
FIG. 2 is a perspective view of the components shown in FIG. 1 in an assembled or storage configuration.
Figure 4:
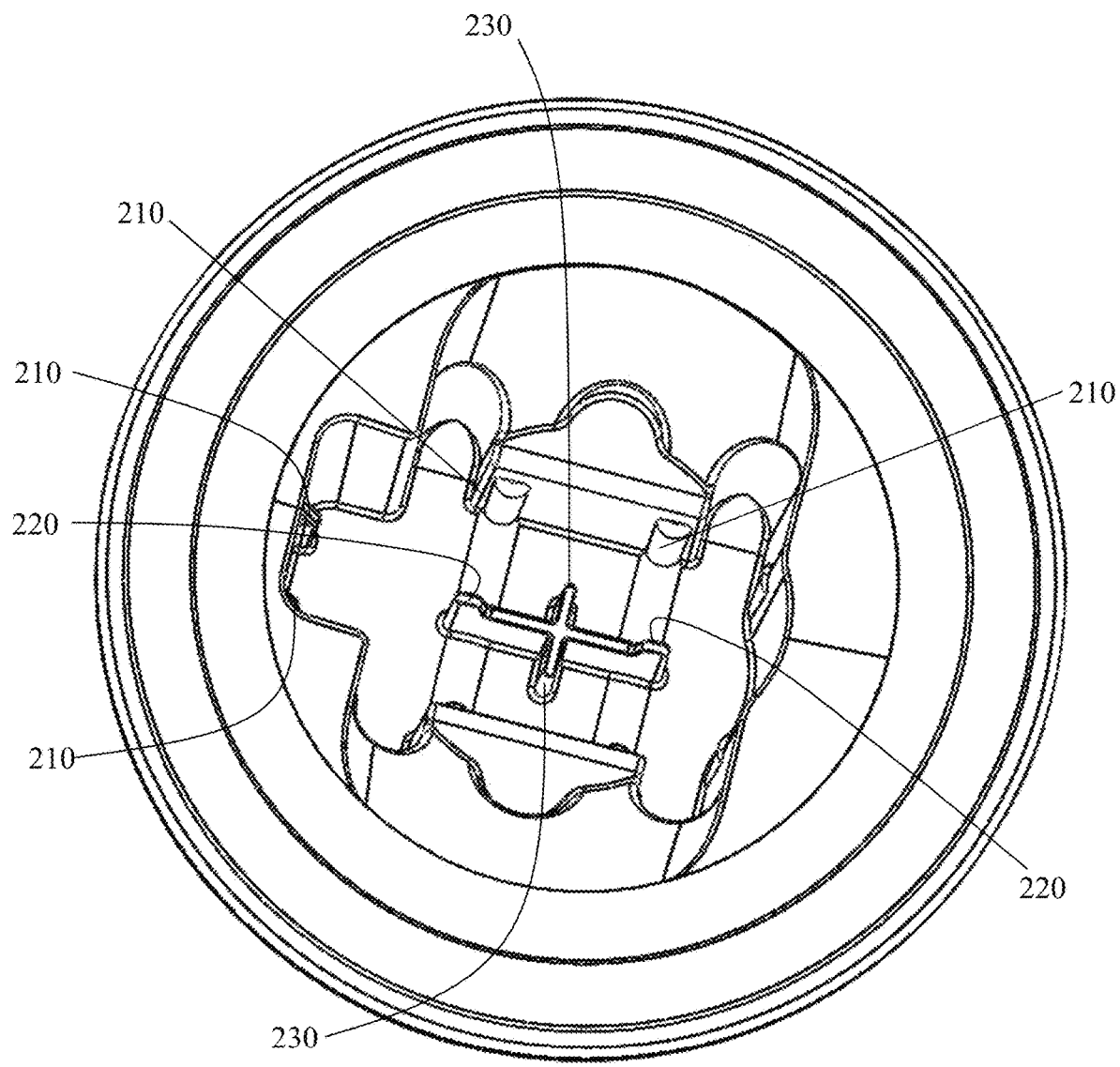
FIG. 4 is an enlarged perspective view of a portion of the vial showing engagement surfaces.
Figure 5:
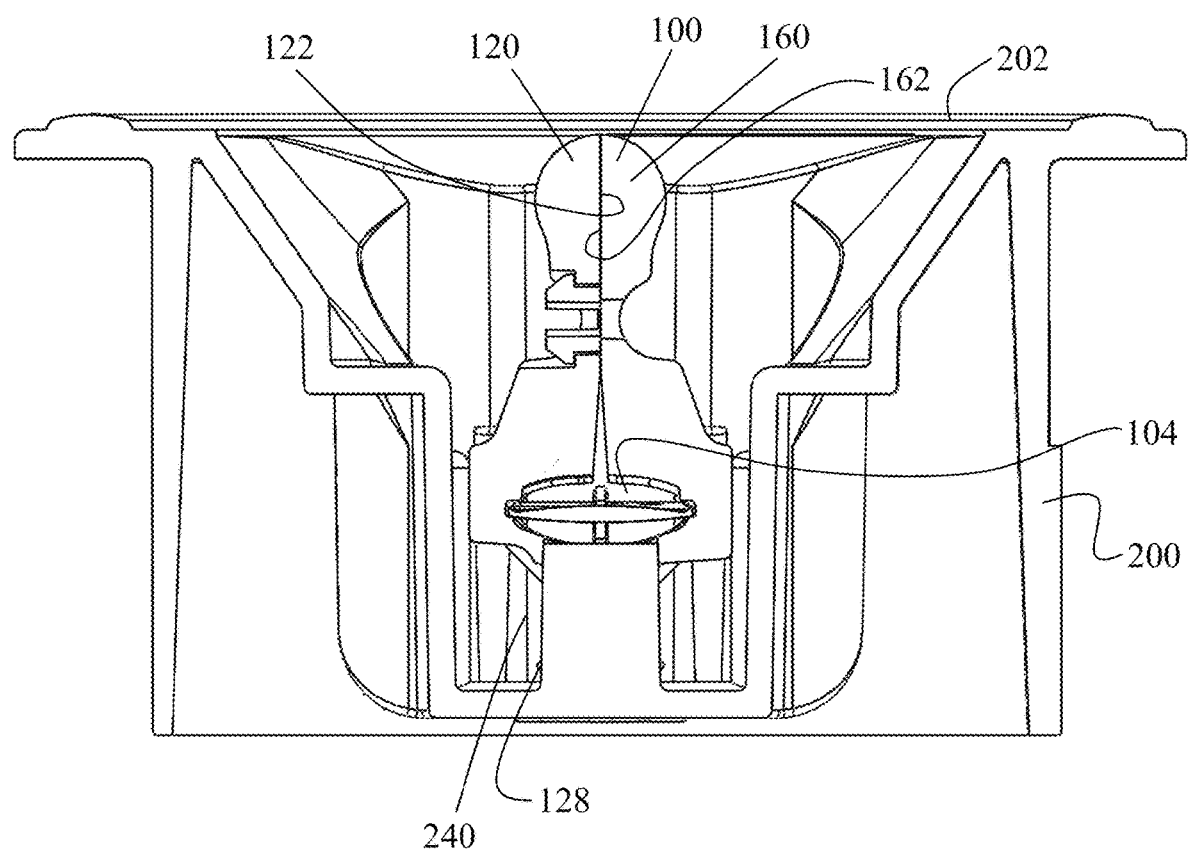
FIG. 5 is a cross sectional view of the shuttle and the IOL in the storage configuration as retained in the vial.
Figure 6:
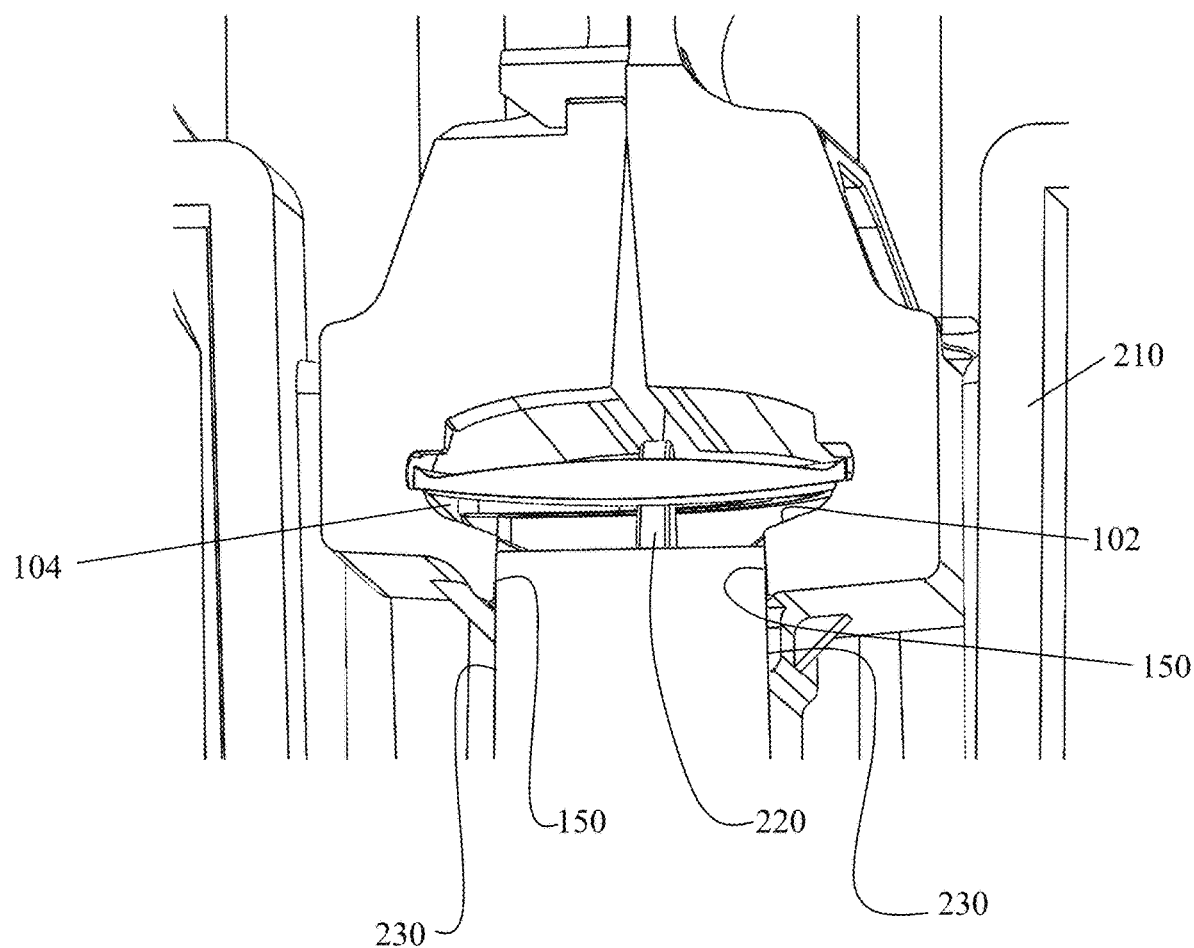
FIG. 6 is a perspective, cross sectional view of the shuttle and the IOL in the storage configuration as retained in the vial.

As seen in FIG. 2, the shuttle 100 is coupled to the vial 200 to preclude unintended separation, wherein the lid 202 seals the vial with the shuttle and IOL inside. Referring to FIGS. 4-6, the vial 200 includes (i) orienting and locating surfaces 210 for orienting the shuttle in the vial, (ii) locating surfaces 220 for locating the IOL within the shuttle and (iii) wedging surfaces 230 to dispose the shuttle in the storage configuration. It is understood, these surfaces can be separate spaced surfaces of the vial 200 or can be incorporated into common surfaces performing a plurality of functions.

The orienting surfaces 210 are configured as elongate ribs for friction fitting with a surface of the shuttle 100, and typically an outer surface of the shuttle. The orienting surfaces 210 function to orient and constrain the shuttle 100 is a predetermined relationship within the vial 200. Further, the orienting surfaces 210 can be sized to provide a friction fit engagement with the shuttle 100 to assist in retaining the shuttle relative to the vial 200.

Figure 7:
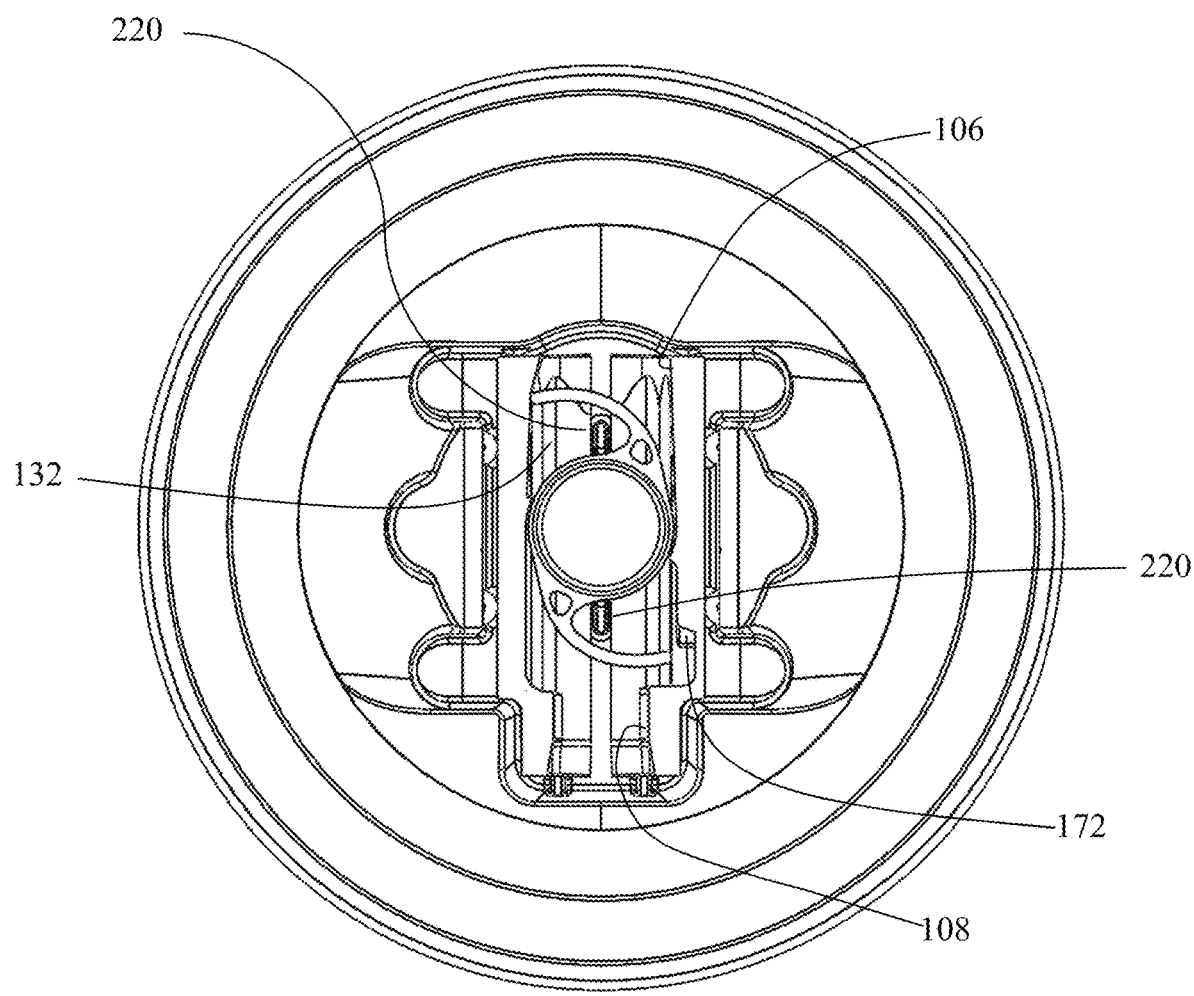
FIG. 7 is a top plan view of a cross sectional of the shuttle and the IOL in the storage configuration as retained in the vial.

The locating surfaces 220 are configured to be disposed within a portion of the shuttle 100 upon the shuttle being operably engaged with the vial 200. The locating surfaces 220 bound or limit movement of the IOL 10 within the shuttle 100. As seen in FIGS. 2, 6 and 7, the locating surfaces 220 project into the shuttle 100 to limit or bound movement of the IOL 10 within the shuttle upon operable engagement of the shuttle with the vial 200.

The wedging surfaces 230 of the vial 200 are configured to urge or force the shuttle 100 to a storage configuration, such as the engaged or coupled storage configuration, upon operable engagement of the shuttle and the vial.

The lid 202 seals the vial 200 by any of a variety of mechanisms known in the art to retain the solution within the vial.

The surfaces of the vial 200 in conjunction with the lid are configured to engage and retain the shuttle 100 relative to the vial so as to preclude unintended displacement of the shuttle and restrict the shuttle in the vial from compressing or deforming the IOL 10 during intended storage and transportation.

Thus, the vial 200 is constructed to engage, and dispose the shuttle 100 to a storage configuration and retain the shuttle in the storage configuration, wherein an IOL optic 16 is maintained in a nominal, unstressed, state.

Shuttle

The shuttle 100 includes a first shuttle plate 120 and a second shuttle plate 160, wherein the first and the second shuttle plates are configured to operably engage and define (i) a shuttle lumen 102 having an IOL chamber 104 sized to receive the IOL 10, (ii) a storage set of confronting surfaces 122, 162, (iii) a loading set of confronting surfaces 124, 164 and (iv) a flexure interface 126, 166 intermediate the storage set of confronting surfaces and the loading set of confronting surfaces, such that portions of the operably engaged first and second shuttle plates flex about the flexure interface between (a) a storage configuration, such as an engaged or coupled storage configuration, wherein the storage set of confronting surfaces abut and the loading set of confronting surfaces are spaced apart and (b) a loading configuration, such as an engaged or coupled loading configuration, wherein both the storage set of confronting surfaces and the loading set of confronting surfaces abut. The terms storage configuration and loading configuration are intended to encompass engaged or coupled storage configuration and engaged or coupled loading configuration, respectively.

As used in connection with the description of the engaged shuttle plates 120, 160 flexing or moving between and assuming the different arrangements or relative positions, the term configuration is intended to encompass the different arrangements or relative positions of the shuttle plates, when the shuttle plates are flexed relative to each other while engaged, as set forth below. Further, the term abut means next or adjacent to, having a common boundary or in contact.

Figure 11:
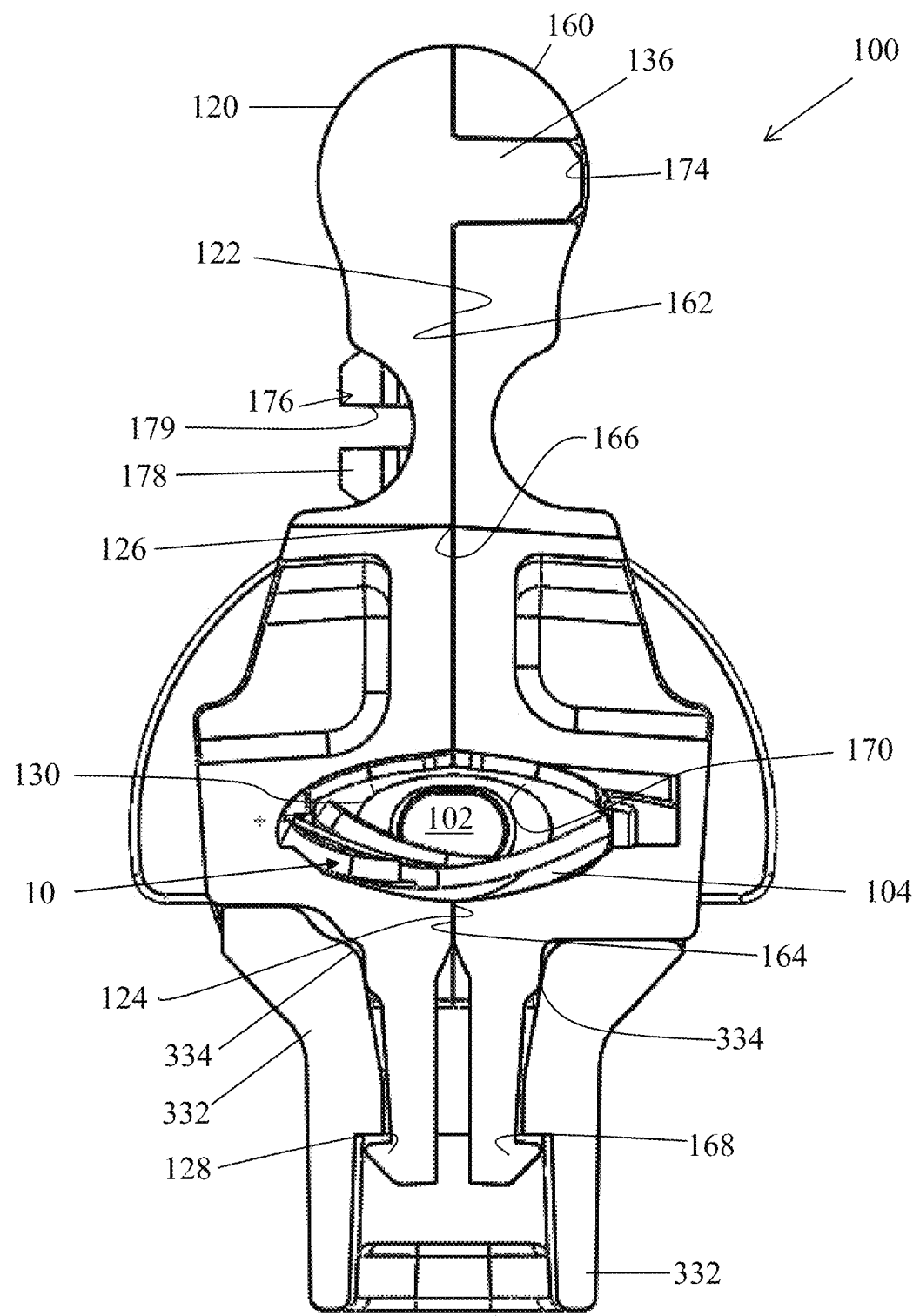
FIG. 11 is a cross sectional view of the shuttle and the IOL in the loading configuration as retained in the injector.
Figure 14:
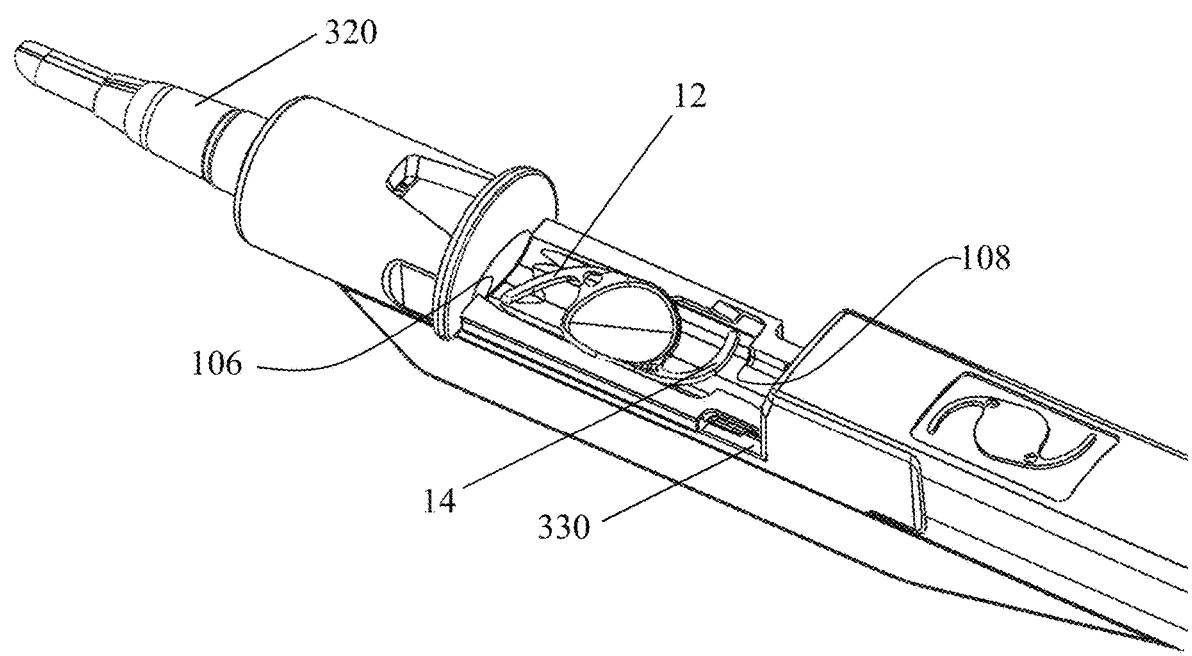
FIG. 14 is a perspective, cross sectional view of the IOL and a portion of the shuttle in the loading configuration as retained in the injector.

As seen in FIG. 11, each shuttle plate 120, 160 includes a recess 130, 170 defining a portion of the shuttle lumen 102 and the IOL chamber 104, a distal port 106 and a proximal port 108, shown in FIG. 14. The shuttle lumen 102 extends along the longitudinal axis. Referring to FIG. 11, each shuttle plate 120, 160 thus includes the corresponding storage confronting surface 122, 162, the loading confronting surface 124, 164, and the flexure interface 126, 166.

Figure 15:
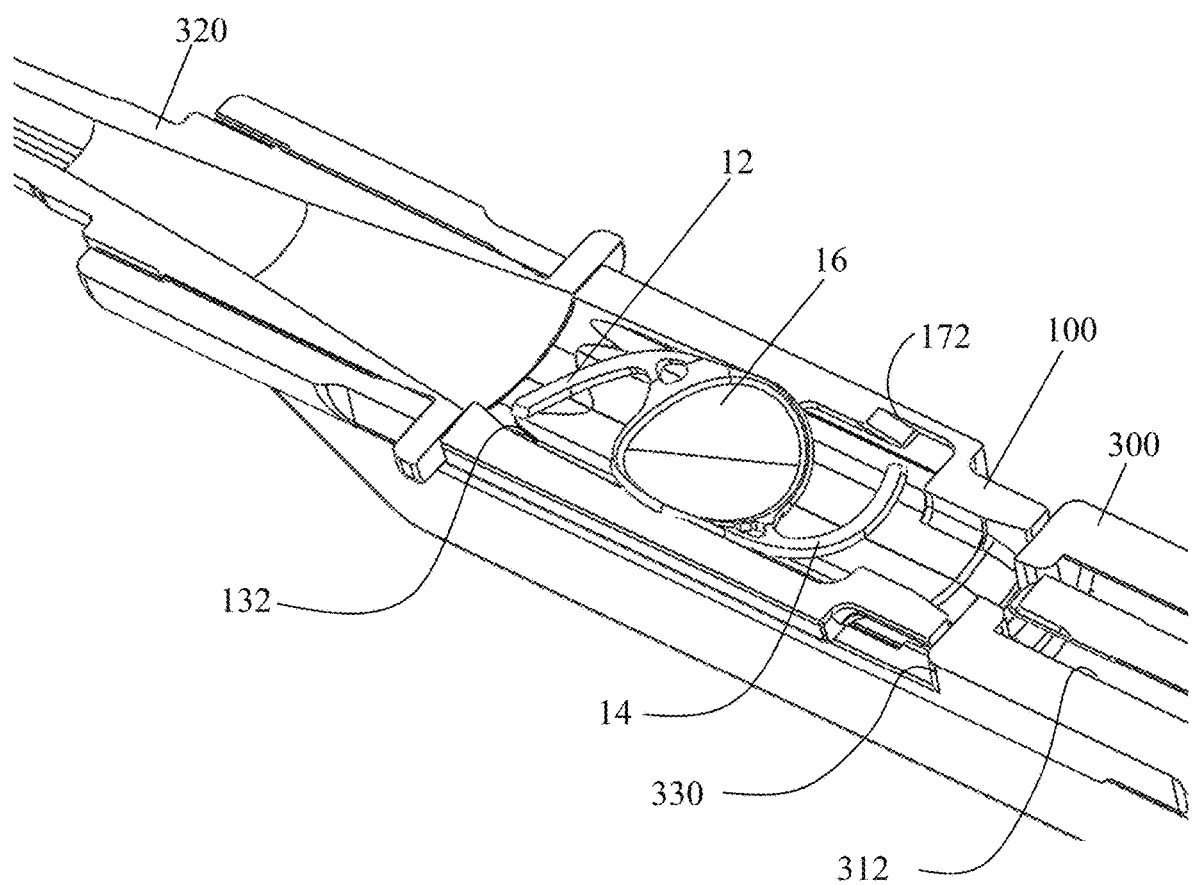
FIG. 15 is an enlarged perspective, cross sectional view of the IOL and a portion of the shuttle in the loading configuration as retained in the injector.
Figure 16:
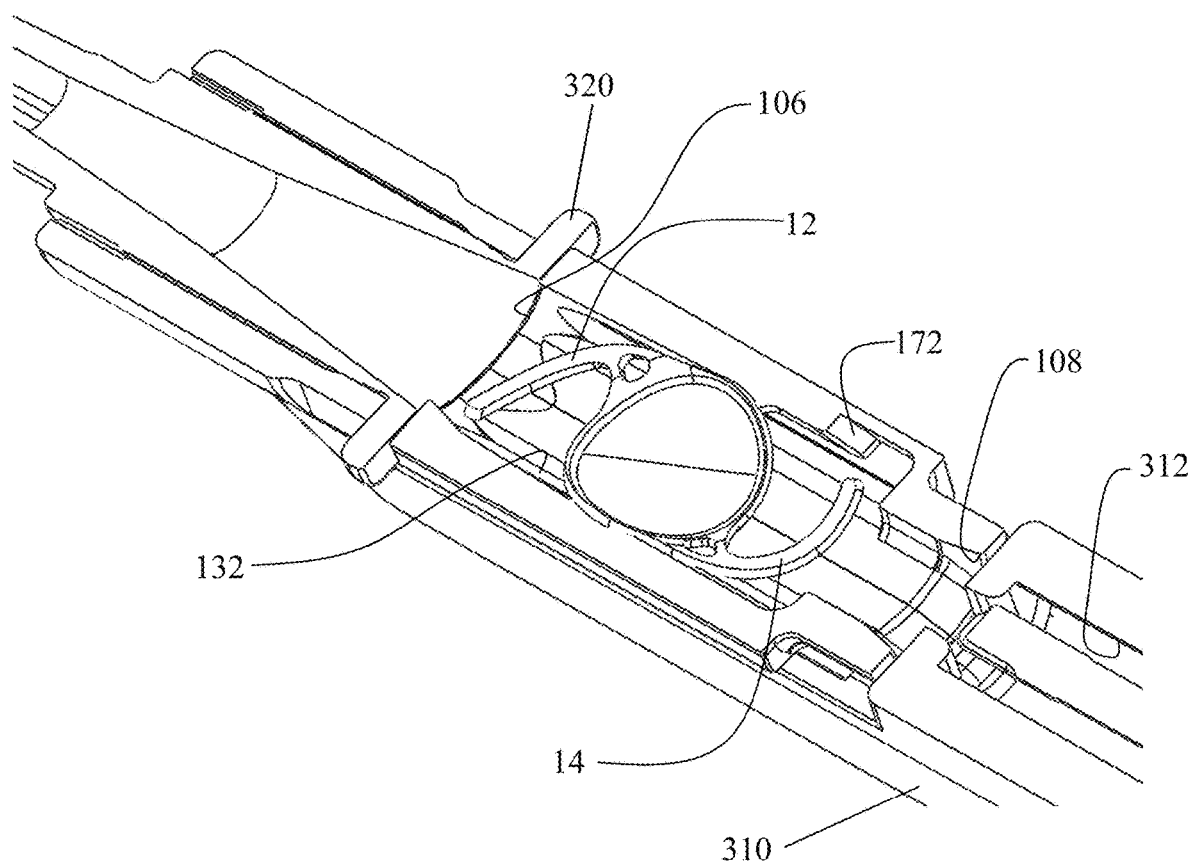
FIG. 16 is an enlarged perspective, cross sectional view of the IOL and a portion of the shuttle in the loading configuration as retained in the injector with the plunger assembly advanced.

Referring to FIGS. 15 and 16, each recess 130, 170 defining the portion of the IOL chamber 104 includes a haptic ramp 132, 172, thereby disposing the haptic ramp in the IOL chamber upon operable engagement of the shuttle plates 120, 160. The haptic ramp 132, 172 defines an included surface in the IOL chamber 104, wherein the haptic ramp is inclined along and relative to the longitudinal axis. In one embodiment, the incline of each haptic ramp 132, 172 locates an end of the ramp substantially coplanar or above an adjacent portion of the optic 16 of the IOL 10 refrained in the shuttle 100. The incline is sufficient to cause at least a portion of each haptic 12, 14 to overlay the optic 16 as the IOL 10 is urged by the injector 300 from the IOL chamber 104. Thus, each haptic ramp 132, 172 is located to contact a corresponding haptic 12, 14 upon translation of the IOL 10 along the longitudinal axis in the shuttle lumen 102. As set forth below, movement of the IOL 10 in response to the injector can include a deformation or movement of the haptics 12, 14 which causes the haptics to contact a corresponding haptic ramp 132, 172, and upon further movement of the IOL 10 the haptics travel up the ramps to the overlying position with respect for the optic 16 of the IOL.

Figure 13:
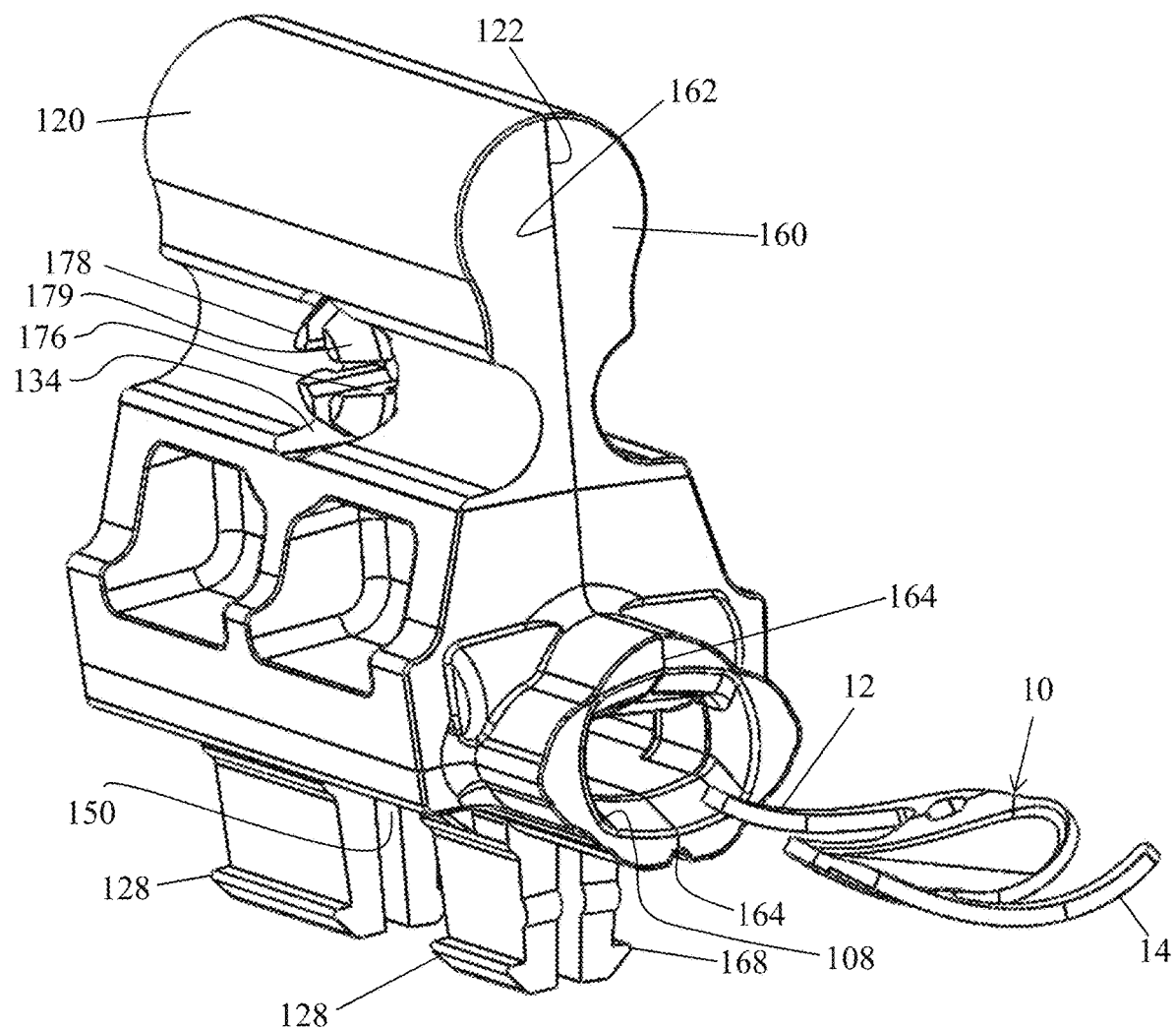
FIG. 13 is an exploded perspective view of the IOL in the shuttle in the loading configuration.

As seen in FIGS. 11 and 13, the storage confronting surface 122, 162 and the loading confronting surface 124, 164 of each shuttle plate 120, 160 extends the length of the shuttle plate along the longitudinal direction. However, it is understood the storage confronting surface 122, 162 and the loading confronting surface 124, 164 of each shuttle plate 120, 160 can effectively be reduced to half the length of the shuttle plate as well as to a point of contact between the first shuttle plate and the second shuttle plate.

In one embodiment of the shuttle plates 120, 160, the storage set of confronting surfaces 122, 162 are parallel and the loading set of confronting surfaces 124, 164 are non-parallel in the first or storage configuration in of the shuttle 100. In this embodiment of the shuttle plates 120, 160, the storage set of confronting surfaces 122, 162 remain parallel and the loading set of confronting surfaces 124, 164 are flexed to a parallel orientation in the second or loading configuration of the shuttle 100.

The flexure interface 126, 166 is the interface for the flexing or hinging of the shuttle plates 120, 160 and specifically pivoting the loading set of confronting surfaces 124, 164 relative to the storage set of confronting surfaces 122, 162. The flexure interface 126, 166 can be points of contact, a line of contact or contacting two-dimensional areas. Referring to FIG. 11, the flexure interface 126, 166 is defined by surfaces that are intermediate the storage confronting surfaces 122, 162 and the loading confronting surface 124, 164 of each shuttle plate 120, 140 along a directional transverse to the longitudinal axis.

The flexure interface 126, 166 can provide for flexing of portions of the shuttle plates 120, 160 (and particularly the loading set of confronting surfaces 124, 164) about an axis, wherein the axis is generally parallel to the longitudinal axis. It is further understood the flexing of the shuttle plates 120, 160 can include a rocking movement or relationship, wherein the movement is of an arcuate or concave surface against another surface which can be arcuate, planar, concave or convex. Thus, rather than a line or axis of flexure, the flexing relationship can include movement along an area of the flexure interface 126, 166.

Thus, along a direction transverse to the longitudinal axis, the flexure interface 126, 166 or surface, is intermediate the storage set of confronting surfaces 122, 162 and the loading set of confronting surfaces 124, 164. Accordingly, the IOL chamber 104 is intermediate the storage set of confronting surfaces 122, 162 and the loading set of confronting surfaces 124, 164 along a direction transverse to the longitudinal axis.

Each shuttle plate 120, 160 also includes a retaining tab 128, 168 moveable between a nominal, relaxed position and a flexed position. The retaining tabs 128, 168 are configured to engage and lock in the injector 300, and in one configuration preclude nondestructive separation of the shuttle 100 from the injector. Conversely, the engagement of the shuttle 100 and vial 200 is constructed to permit selectively disengagement of the shuttle from the vial. While each shuttle plate 120, 160 is shown having two retaining tabs 128, 168, it is contemplated each shuttle plate can include one or three or more retaining tabs. It has been found satisfactory for each shuttle plate 120, 160 to include two longitudinally spaced retaining tabs 128, 168.

Figure 3A:
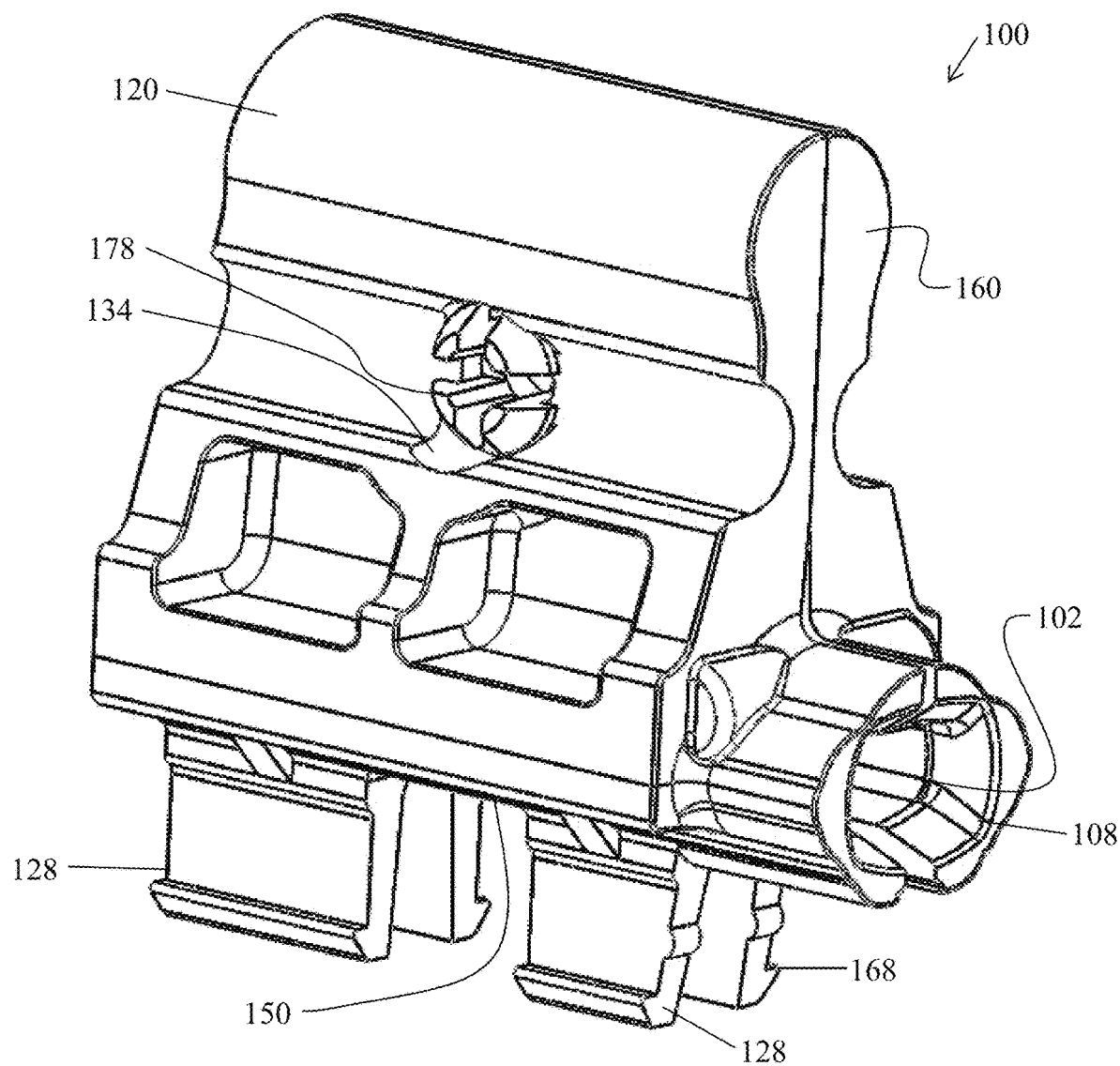
FIG. 3a is a perspective view of the shuttle shown in FIG. 1 in a storage configuration.
Figure 3B:
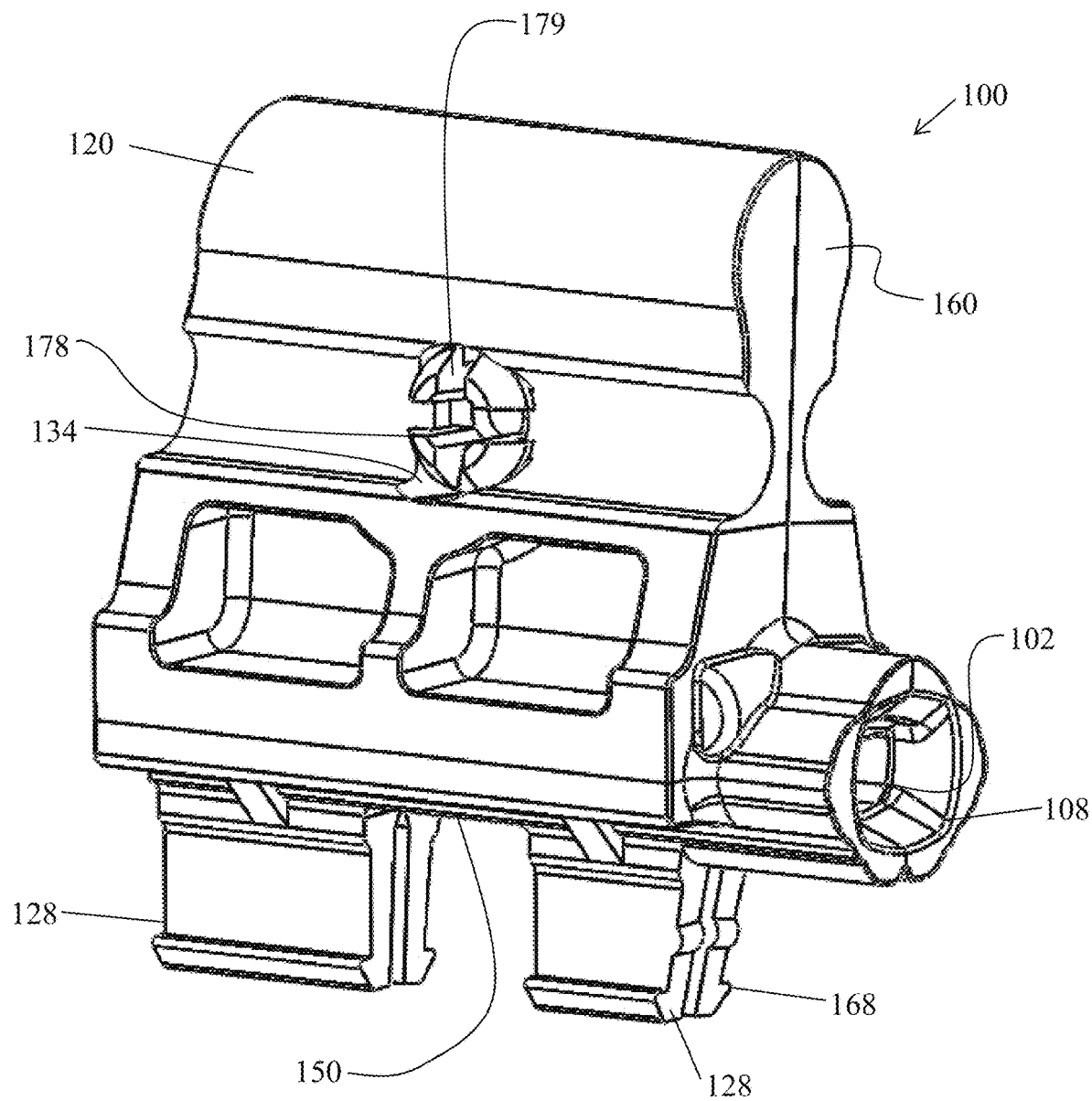
FIG. 3b is a perspective view of the shuttle shown in FIG. 1 in a loading configuration.

The first and the second shuttle plates 120, 160 also define an access port 150, as shown in FIGS. 3a and 3b, used in loading the IOL 10 within the shuttle 100. The access port 150 can be transverse to the longitudinal axis of the shuttle lumen 102 and accesses or opens to the IOL chamber 104. The access port 150 has a major dimension, or diameter, which is less than the IOL 10 or at least the optic 16 of the IOL so as to substantially preclude passage of the IOL through the access port under intended operating conditions. While the access port 150 is shown as independent of the distal port 106 and the proximal port 108, it is understood that depending on the construction of the fixture set forth below one of the distal port and the proximal port can function as the access port.

The shuttle plates 120, 160 further include an interconnect structure for interconnecting the shuttle plates while allowing relative movement, such as flexing of the loading set of confronting surfaces 124, 164 of the shuttle plates between the storage configuration and the loading configuration. Referring to FIGS. 3b and 11, in one embodiment of the interconnect structure, each shuttle plate 120, 160 includes a receiving hole 134, 174 and a mating post 136, 176, wherein the receiving hole of the first shuttle plate 120 receives the mating post of the second shuttle plate 160 and the receiving hole of the second shuttle plate receives the mating post of the first shuttle plate. This embodiment can further provide one of the mating posts such as 176 having flexible capture tabs 178 defined by adjacent gaps 179, wherein the length of the mating post and thickness of the shuttle plate at the receiving hole are configured to provide that the capture tabs are flexed to a compressed state to pass entirely through the hole and then expand to the relaxed state, wherein the capture tabs are spaced from the outer surface of the shuttle plate, thereby allowing relative movement of the engaged or coupled shuttle plates. Alternatively, the capture tabs are sized to be located adjacent to or in contact with the outer surface of the receiving shuttle plate, thereby retaining the storage set of confronting surfaces 122, 162 in an abutting orientation in both the storage configuration and the loading configuration of the shuttle 100. By sizing the capture tabs 178 and amount of compression necessary to pass through the receiving hole 134, passage of the capture tabs back through the receiving hole is precluded—thereby providing for non-destructive separation of the coupled or engaged shuttle plates 120, 160. That is, non-destructive separation of the engaged or coupled shuttle plates 120, 160 is precluded by configuring the capture tabs 178 and the receiving hole 136, and the amount of compression necessary to pass through the receiving hole. Alternatively, the shuttle plates 120, 160 can be configured to permit non-destructive separation.

The remaining mating post and receiving hole, such as 136 and 174 are configured to function as a guide for the relative engagement of the shuttle plates 120, 160. That is, the remaining mating post and receiving hole provide that the engaged shuttle plates 120, 160 can only flex about the flexure interface 126, 166 parallel to the longitudinal axis. The engagement of the remaining post and receiving hole (i) prevent the engaged shuttle plates from spinning about the engagement of the first mating post and the first receiving hole and (ii) permit flexing of the portions of the shuttle plates 120, 160 about the flexure interface 126, 166.

Referring to the FIGS. 3b and 11, the shuttle plates 120, 160 are operably interconnected, such as engaged or coupled by aligning each mating post 136, 176 with the respective receiving hole 134, 174 and pressing the shuttle plates together, thereby compressing the mating post having the capture tabs to a cross section sufficiently small to pass the mating post with the capture tabs through the corresponding receiving hole of the remaining plate, until the capture tabs pass through the corresponding shuttle plate, expand and couple or engage the shuttle plate. In the configuration of the capture tabs 178 being spaced from the outside surface of the shuttle plate receiving the tabs, the shuttle plates 120, 160 can be rocked, while in an engaged or coupled state. In the configuration of the capture tabs 178 contacting the outside surface of the receiving shuttle plate, the storage set of confronting surfaces 122, 162 are retained in an abutting relationship in each configuration of the shuttle 100, as shown in FIGS. 3a and 5. The remaining mating post and corresponding receiving hole such as 136 and 174 guide the relative motion of the shuttle plates 120, 160 about the flexure interface. The engagement or coupling of the shuttle plates 120, 160 includes the connection or interconnection of the otherwise separate components to form the operable shuttle 100.

The first and the second shuttle plates 120, 160 are separate independent elements. That is, the shuttle plates 120, 160 are not joined or connected prior to their engagement to form the shuttle 100. There is no integral connection of the shuttle plates 120, 160 before the individual shuttle plates are interconnected to form the shuttle 100. The shuttle plates 120, 160 being independent means the shuttle plates are separate elements which are interconnected, such as by being coupled or engaged, only as part of the assembling or formation of the shuttle 100. It is contemplated the first and the second shuttle plates 120, 160 are individually formed and form the IOL chamber 104 only upon coupling or engagement of the separate shuttle plates. Thus, the term separate means discrete, independent components that are not integrally connected or joined.

Upon operable engagement or coupling of the shuttle plates 120, 160, the resulting shuttle 100 defines the shuttle lumen 102 having the IOL chamber 104 for retaining the IOL 10, wherein the IOL chamber is bounded along the longitudinal axis by the proximal port 108 and the distal port 106. The haptic ramps 132, 172 are thus located in the IOL chamber 104. By retaining the IOL 10, the IOL chamber 104 forms a container that captures the IOL, wherein the IOL cannot pass from the chamber in any direction without deformation from a nominal state, and in select embodiments without deformation of the optic 16 of the IOL. In select embodiments, the IOL chamber 104 is entirely defined by the first and the second shuttle plates 120, 160.

The distal port 106 and the proximal port 108 are sized to pass a portion of the injector 300. In one embodiment, the distal port 106 and the proximal port 108 define a continuous periphery, wherein the periphery of each port lies in a corresponding plane. However, as seen in the Figures, the periphery of each the distal port 106 and the proximal port 108 can extend along a dimension of the longitudinal axis. That is, the periphery of each of the distal port 106 and the proximal port 108 does not lie in a single plane, but rather extends a distance along the longitudinal axis. In the loading configuration, at least the bottom of the shuttle lumen defines a substantially continuous surface. That is, the bottom is free of gaps or spacings between the shuttle plates that would detrimentally interfere with the movement of the IOL 10 along and from the shuttle lumen. As the IOL 10 is preferentially curved along the bottom of the shuttle lumen, a top portion of the lumen at the proximal end need not be continuous. It is advantageous in deforming the IOL 10 to a presentation configuration that the distal end of the top of the shuttle lumen 102 be a sufficiently continuous surface to preclude detrimental engagement with the IOL as the IOL passes the distal port.

The distal port 106 and the proximal port 108 have a major dimension transverse to the longitudinal axis. As seen in the FIGS. 5, 6 and 11, the distal port 106 and the proximal port 108 can have a non-circular, elliptical or oval cross section. In such embodiments, the major dimension is the largest dimension transverse to the longitudinal axis which is bounded by the periphery of the port.

As set forth above, the interconnection of shuttle plates 120, 160 permits the relative flexing, or pivoting, of the loading set of confronting surfaces 124, 164 of the shuttle plates, while the shuttle plates remain in an interconnected, coupled or engaged, configuration. Specifically, with the engaged first and second shuttle plates 120, 160, the loading set of confronting surfaces 124, 164 can be flexed about the flexure interface between (i) a storage configuration, wherein the storage set of confronting surfaces 122, 162 abut and the loading set of confronting surfaces 124, 164 are spaced apart and (ii) a loading configuration, wherein the storage set of confronting surfaces remain abutting while the loading confronting surfaces are pivoted about the flexure interface to abut.

The IOL chamber 104, existing and defined and operable in both the storage configuration of the shuttle 100 and the loading configuration of the shuttle, changes a dimension for retaining the IOL 10 as the shuttle is configured between the storage configuration and the loading configuration. Specifically, the IOL chamber 104 defines (i) a storage dimension transverse to the longitudinal axis for the optic 16 of the IOL 10 in the storage configuration and (ii) a loading dimension transverse to the longitudinal axis for the optic of the IOL in the loading configuration, wherein the loading dimension is smaller than the storage dimension. In one embodiment, the storage dimension is sufficient to retain at least the optic 16 of the IOL 10 in a nominal state. The loading dimension and surfaces defining the IOL chamber 104 are selected such that upon the shuttle 100 being disposed in the loading configuration, the optic 16 of the IOL 10 is preferentially deformed or curved to a substantially predetermined shape.

Injector

Figure 8:
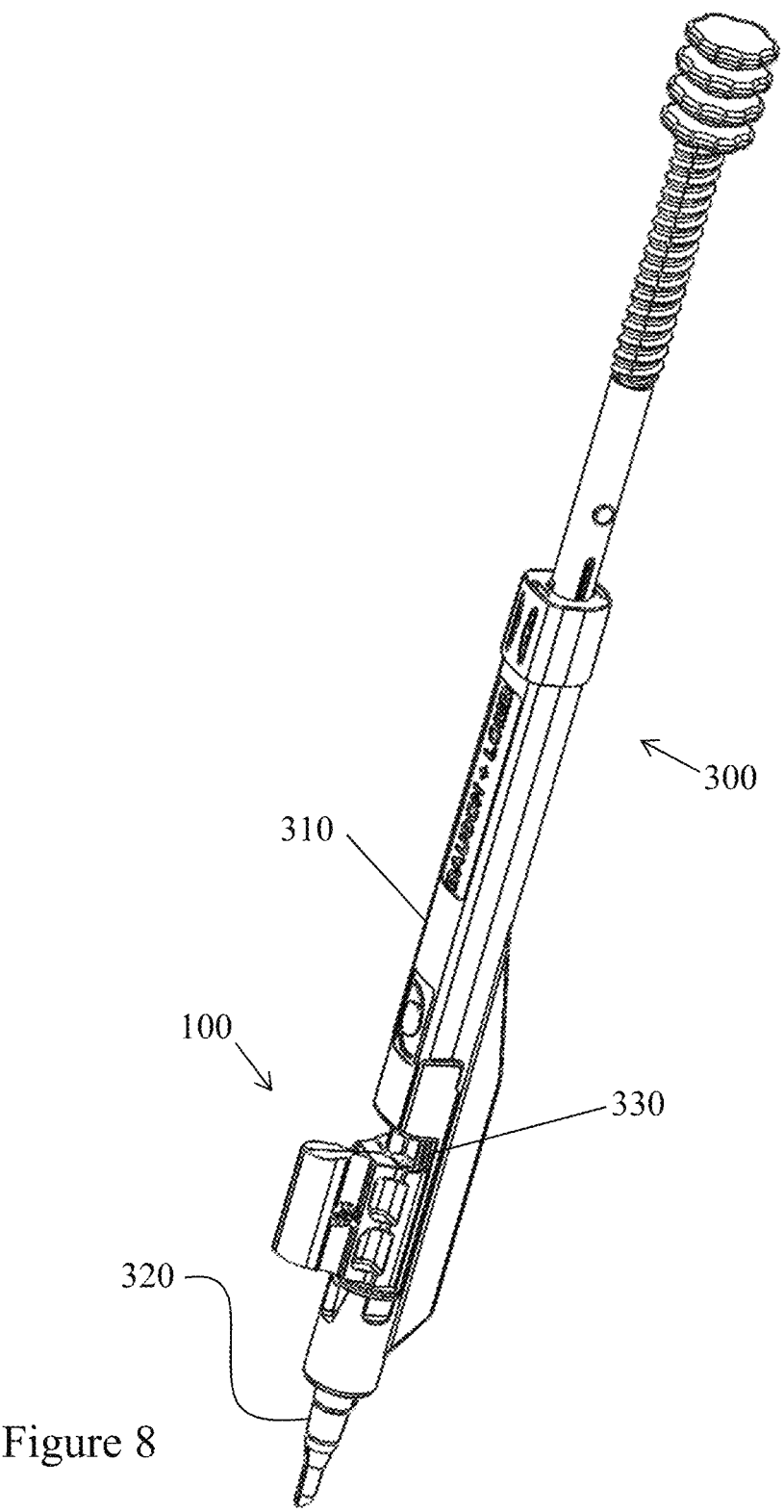
FIG. 8 is a perspective view of the shuttle operably engaged with an injector.
Figure 9:
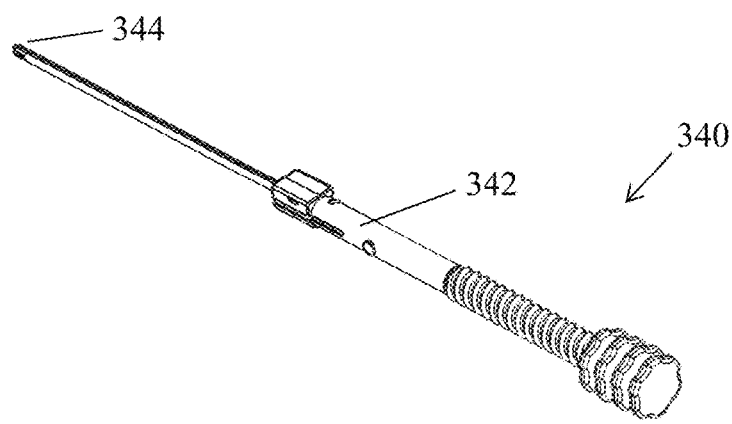
FIG. 9 is a perspective view of a plunger assembly of the injector.
Figure 10:
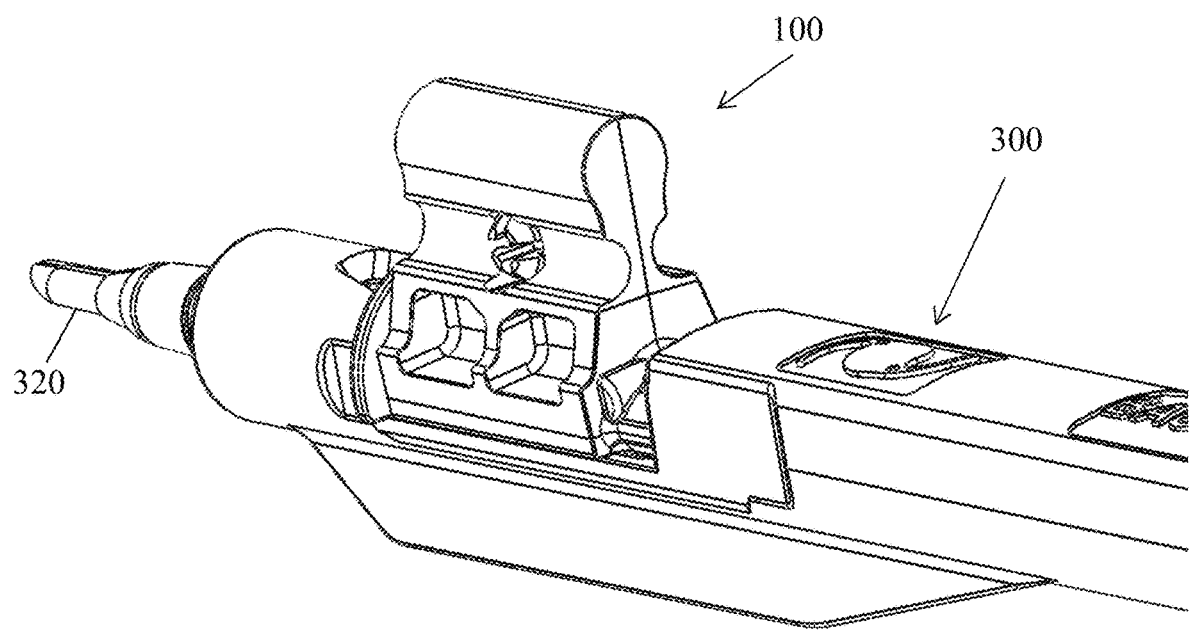
FIG. 10 is a perspective view of the shuttle operably engaged with an injector.

The representative injector 300 is shown in FIG. 8. The injector 300 includes an injector body 310 having a lumen 312, seen in FIGS. 15 and 16, extending along the longitudinal axis from a proximal end to distal end. The lumen 312 can have any of a variety of cross-sectional profiles, wherein circular or oval shapes are typical. The proximal end of the injector body 310 may include a finger hold flange preferably configured with an edge as shown for resting the injector on a flat surface. It is understood that the overall structure of the injector body 310 may vary from that shown and described herein. It is furthermore understood that the components of the injector 300 may be made of any suitable material (e.g., polypropylene) and may be wholly or partly opaque, transparent or translucent to better visualize the IOL within the injector device and the IOL delivery sequence.

In one embodiment, the injector body 310 further cooperates with an injector tip 320 which defines an extension of the lumen so as to define a pathway of the IOL 10 from the shuttle 100 to the eye of the patient. The injector tip 320 defines a terminal end of a size for insertion or presentation to the eye, with the IOL 10 correspondingly deformed within the injector tip. However, it is understood, the injector body 310 can include an integral injector tip or nozzle defining a portion of the lumen for directing the IOL 10 from the shuttle to the eye of the patient.

Referring to FIGS. 10, 11, 12 and 14-16, the injector body 310 further includes a shuttle bay 330 opening into the lumen 312. The shuttle bay 330 receives or accepts the shuttle 100 for operable engagement with the injector 300. The shuttle bay 330 includes engaging surfaces 332 for engaging the shuttle 100. The engaging surfaces 332 can include alignment surfaces for contacting the shuttle 100 in predetermined locations to provide accurate and reproducible retention of the shuttle in the injector 300.

Figure 12:
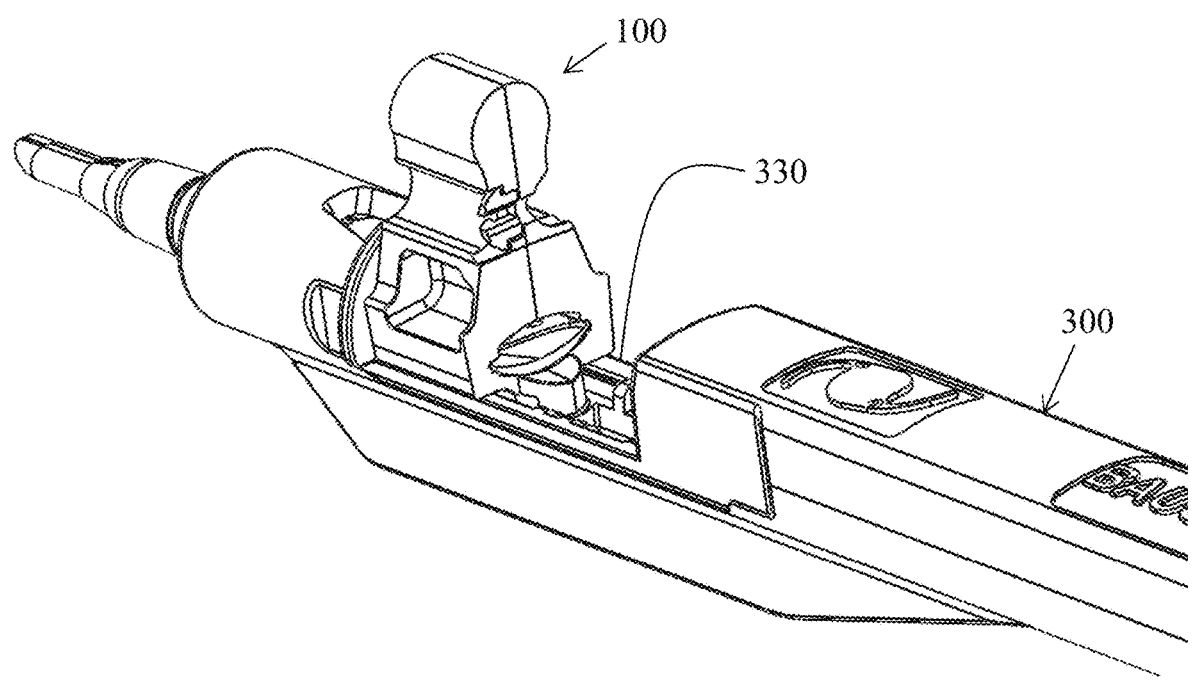
FIG. 12 is a perspective, cross sectional view of the shuttle and the IOL in the loading configuration as retained in the injector.

The shuttle bay 330 also includes camming surfaces 334 that flex or pivot the loading set of confronting surfaces 124, 164 of the engaged shuttle plates 120, 160 from the storage configuration to the loading configuration. As seen in FIGS. 11-13, upon being disposed in the loading configuration, the storage set of confronting surfaces 122, 162 remain substantially as in the storage configuration and the loading set of confronting surfaces 124, 164 are flexed to abut.

The injector 100 is shown as employing a user imparted actuation force for moving the IOL 10 from the shuttle 100 and into the eye.

Referring to FIGS. 8-10 and 15, 16, the injector 100 includes a plunger 340 having a plunger shaft 342 and a plunger tip 344 configured for engaging the IOL 10 and specifically the optic 16 at the periphery of the optic as the plunger is advanced along the shuttle lumen 102. It is understood that other plunger tip designs may be used with the present system as desired. In one embodiment, the plunger shaft 342 is rotationally fixed within lumen 312 to prevent unexpected rotation of the plunger shaft (and thus the plunger tip) with the lumen. The plunger shaft 342 may be rotationally fixed by forming the proximal shaft length and lumen non-circular in cross-section or by including rotational fixing elements on the lumen inner wall and plunger shaft (e.g., longitudinal flange on the plunger having a sliding fit within a longitudinally extending groove provided on the lumen inner wall).

Operation

After manufacture of the IOL 10, the IOL is releasably retained on a fixture. The fixture can be any of a variety of constructions that can retain and repeatedly locate an IOL 10 without damage to the IOL. In one embodiment, the fixture is a mount fixed at an end of an elongate shaft, wherein the mount and a portion of the elongate shaft can be passed through the access port 150 of the shuttle 100. The orientation of the mounted IOL can be aby of a variety of orientations, such as but not limited to orienting the IOL 10 such that an optical axis of the IOL is perpendicular to or parallel to the shuttle lumen 102.

As the IOL 10 is retained on the fixture, the first shuttle plate 120 and the second shuttle plate 160 are brought together and interconnected, such as engaged or coupled, about the retained IOL so as to form the IOL chamber 104 about the retained IOL, wherein the a portion of the fixture is disposed within the access port 150. As the shuttle plates 120, 160 are engaged as set forth above, thereby capturing the IOL 10 in the IOL chamber 104, the IOL is released from the fixture and the fixture is withdrawn through the access port 150, leaving the IOL retained in the shuttle 100.

In one configuration, the IOL 10 is oriented within the IOL chamber 104 such that one haptic 12 is adjacent or towards the distal port 106 thereby defining a leading haptic and the remaining haptic 14 is adjacent or towards the proximal port 108 thereby defining a trailing haptic as oriented within the IOL chamber 104 of the shuttle 100.

When the shuttle 100 is unconstrained in either the vial 200 or the injector 300, the IOL chamber 104 captures the IOL 10 and precludes exiting of the IOL under intended operating parameters. In each of the engaged storage and the engaged loading configuration of the shuttle plates 120, 160, passage of the IOL 10 from the shuttle 100 is inhibited by the size of the distal and proximal ports 106, 108 and the access port 150 relative to the size of the IOL (or at least the size of the optic 16 of the IOL).

The shuttle 100 carrying the retained IOL 10 is then engaged with the vial 200. Upon engagement of the shuttle 100 with the vial 200, the orienting surfaces 210 of the vial contact select exposed surfaces of the shuttle to orient the shuttle in the vial.

The locating surfaces 220 of the vial 200 project into the IOL chamber 104 for locating the IOL 10 within the shuttle 100, as seen in FIGS. 5-7. Thus, the IOL 10 is at least partly located within the IOL chamber 104 by surfaces in addition to the surfaces of the engaged shuttle plates 120, 160 that define the IOL chamber.

The wedging surfaces 230 of the vial 200 contact the shuttle plates 120, 160 to dispose the shuttle 100 in the storage configuration. That is, the wedging surfaces 230 contact surfaces 150 on both shuttle plates and impart or ensure the loading set of confronting surfaces 124, 164 are spaced apart, such that the IOL chamber 104 does not bend or fold the IOL 10. Thus, the storage set of confronting surfaces 122, 162 remain in an abutting position and the loading confronting surfaces 124, 164 to a spaced or separated position. As seen in FIGS. 5-7, the IOL chamber 104 then retains the IOL 10 without any material deformation or stress to the optic 16 of the IOL, such that the optic is in a nominal state and in select embodiments without any material deformation or stress to the optic and the haptics 12, 14.

The distal port 106 and the proximal port 108 having a smaller dimension than the IOL 10 (or at least the optic 16 of the IOL) preclude passage of the IOL from the IOL chamber 104 through the ports. Similarly, the access port 150 has a dimension to preclude passage of the IOL 10 under intended operating parameters. Absent an external removal force, such as the plunger acting on the IOL 10, the IOL chamber 104 retains the IOL within the chamber in both the engaged storage configuration of the shuttle (the engaged first and second shuttle plates 120, 160) and the engaged loading configuration of the shuttle (the engaged first and second shuttle plates).

Thus, as the shuttle 100 is engaged with the vial 200, the storage set of confronting surfaces 122, 162 are abutting; the loading set of confronting surfaces 124, 164 are spaced apart. The orienting surfaces 210 of the vial 200 contact the outer surfaces of the shuttle 100 to position and retain the shuttle within the vial. The wedging surfaces 230 of the vial 200 contact the surfaces 150 of the shuttle 100 to maintain the loading set of confronting surfaces 124, 164 in the nominal spaced apart relation to dispose the shuttle in the storage configuration and the locating surfaces 220 of the vial 200 project into the IOL chamber 104 and limit movement or contact a periphery of the IOL 10 and locate the IOL within the IOL chamber.

The loaded shuttle 100 is retained in the vial 200, sterilized and packaged with a volume of sterile solution. As the IOL 10 is in an unstressed, nominal state, the only limitation on the duration of the storage is the duration of the sterile conditions/packaging.

For presenting the IOL 10 to the patient, the lid 202 is removed from the vial 200, thereby exposing the shuttle 100 as it is retained in the vial. The shuttle 100 is disengaged from the vial 200.

The shuttle 100 is then engaged with the injector 300 by engaging the retaining tabs 128, 168 of the shuttle with the engaging surfaces 332 of the injector. The engaging surfaces 332 or camming surfaces 334 can function as alignment surfaces of the injector 300 and contact corresponding surfaces of the shuttle 100 to operably locate the shuttle 100 in the injector. The camming surfaces 334 are configured to dispose the shuttle 100 in the loading configuration, wherein the loading set of confronting surfaces 124, 164 are flexed or pivoted about the flexure interface and both the storage set of confronting surfaces 122, 162 and the loading set of confronting surfaces 124, 164 abut as seen in FIGS. 11 and 15.

In the loading configuration, the IOL chamber 104 defines a reduced dimension for the optic 16 of the IOL 10, thereby imparting a predetermined bend or curvature to the IOL, as seen in FIGS. 11-16. As set forth below, the predetermined bend or curvature to the IOL 10, ensures that the IOL does not move forward along the shuttle lumen 102 toward the patient eye until the IOL is contacted by the plunger tip 344, which in turn allows the plunger tip to contact the trailing haptic 14 and in conjunction with the corresponding haptic ramp and fold the haptic over the optic 16.

To dispense the IOL 10 from the injector 300, the plunger 340 is actuated causing the plunger tip 344 to enter the shuttle lumen 102 and the IOL chamber 104. The predetermined bend in the optic 16 of the IOL 10 retards movement of the IOL along the shuttle lumen 102. Thus, as the plunger tip 344 first contacts the IOL 10 and specifically the trailing haptic 14, the trailing haptic begins to contact the corresponding haptic ramp and fold over the optic 16. Continued contact by the plunger tip 344 and resistance from the curvature of the optic 16 pushes the trailing haptic 14 up the haptic ramp and folds the trailing haptic over the optic such that the plunger tip then contacts the periphery of the optic. Upon continued contact of the plunger tip 344 and the IOL 10 as the plunger tip advances along the shuttle lumen 102, the leading haptic 12 moves up the corresponding haptic ramp to be disposed above the optic 16.

As the plunger 340 continues to move the IOL 10 along the longitudinal axis and the shuttle lumen 102, the optic 16 of the IOL 10 continues to deform or bend in the direction imparted by the transition of the shuttle 100 from the storage configuration to the loading configuration, and each of the leading and trailing haptics 12, 14 moves up along the respective haptic ramps 132, 172 to dispose a majority of each haptic in an overlying position with respect to the optic.

The plunger 340 continues to move the IOL 10 along the shuttle lumen 102 passing from the shuttle 100 and to the injector tip 320, whereby the IOL can be further deformed to an insertion configuration for presentation to the eye.

Thus, the present shuttle 100 provides for releasably engaging or retaining the IOL 10, wherein the shuttle includes a first component, such as the first shuttle plate 120 and an independent second component, such as the second shuttle plate 160 wherein the first component and the second component define a first set of confronting surfaces and a second set of confronting surfaces and are configured to operably engage so as to define a shuttle lumen 102 extending along the longitudinal axis, the shuttle lumen having the IOL chamber 104 bounded by the proximal port 108 and the distal port 106 on the longitudinal axis; and the operable engagement of the first component and the second component providing (i) a first configuration of the IOL chamber and (ii) a second configuration of the IOL chamber by selectively flexing or pivoting a portion of the engaged shuttle plates about a flexure interface to simultaneously contact the first set of confronting surfaces and the second set of confronting surfaces.

It is contemplated a center line of the optic 16 of the IOL 10 can be located along the longitudinal axis, upon the first shuttle plate 120 and the second shuttle plate 160 being in the first configuration. That is, a midpoint of the optic 16 of the IOL 10 retained within the IOL chamber 104 lies on the longitudinal axis of the lumen. However, it is understood that based on the specific structure of the IOL chamber 104, the midpoint of the optic 16 can be above or below a horizontal plane encompassing the longitudinal axis.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

The invention claimed is:

1. A shuttle for retaining an IOL having an optic, the shuttle comprising:
a first shuttle plate and a separate second shuttle plate operably coupled and configurable between a coupled storage configuration and a coupled loading configuration, the first and the second shuttle plates in each of the coupled storage configuration and the coupled loading configurations defining an IOL chamber extending along a longitudinal axis, the IOL chamber axially bounded by a proximal port and a distal port, wherein each of the proximal port and the distal port in each of the coupled storage configuration and the coupled loading configurations has a major dimension transverse to the longitudinal axis, the major dimension being smaller than a diameter of the optic, the first shuttle plate comprising a first storage confronting surface and a first loading confronting surface, the second shuttle plate comprising a second storage confronting surface and a second loading confronting surface, wherein the first storage confronting surface abuts the second storage confronting surface in the coupled storage configuration and the coupled loading configuration, wherein the first loading confronting surface is spaced from the second loading confronting surface in the coupled storage configuration, and wherein the first loading confronting surface abuts the second loading confronting surface in the coupled loading configuration, wherein the IOL chamber is intermediate (i) the first and second storage confronting surfaces and (ii) the first and second loading confronting surfaces and wherein at least one of the first shuttle plate and the second shuttle plate pivots about a flexure interface intermediate the storage confronting surfaces and the loading confronting surfaces to move the operably coupled first and second shuttle plates from the coupled storage configuration to the coupled loading configuration.

2. The shuttle of claim 1, wherein the IOL chamber has a storage configuration when the first and the second shuttle plates are in the coupled storage configuration and a loading configuration when the first and the second shuttle plates are in the coupled loading configuration.

3. The shuttle assembly of claim 2, wherein the storage configuration of the IOL chamber does not deform the optic of the IOL from a nominal formation.

4. The shuttle assembly of claim 2, wherein the loading configuration of the IOL chamber deforms the optic of the IOL from a nominal formation to a preferential curvature.

5. The shuttle of claim 1, wherein the IOL chamber in each of the coupled storage configuration and the coupled loading configuration of the shuttle captures an IOL.

6. The shuttle of claim 1, wherein the operably coupled first shuttle plate and the second shuttle plate preclude non-destructive separation.

7. The shuttle of claim 1, wherein the IOL chamber is coaxial with a longitudinal axis.

8. The shuttle of claim 1, further comprising a haptic ramp on each of the first and the second shuttle plate, wherein each haptic ramp is sized to displace a haptic to an overlying position with respect to the optic of the IOL.

9. A shuttle for retaining an IOL having an optic, the shuttle comprising:
(a) a first shuttle plate comprising a first storage confronting surface and a first loading confronting surface; and
(b) a separate second shuttle plate comprising a second storage confronting surface and a second loading confronting surface, the second shuttle plate configured to operably engage the first shuttle plate, such that the operably engaged first and second shuttle plates are configured to be disposed between an engaged storage configuration and an engaged loading configuration;
wherein the operably engaged first and second shuttle plates define a shuttle having (i) the first and the second storage confronting surfaces comprising a storage set of confronting surfaces, (ii) the first and the second loading confronting surfaces comprising a loading set of confronting surfaces, (iii) a shuttle lumen extending along a longitudinal axis, the shuttle lumen having an IOL chamber intermediate the storage set of confronting surfaces and the loading set of confronting surfaces, the IOL chamber sized to retain an optic of an IOL, and (iv) a flexure interface intermediate the storage set of confronting surfaces and the loading set of confronting surfaces,
wherein the storage set of confronting surfaces abut in each of the engaged storage configuration and the engaged loading configuration, and the loading set of confronting surfaces flex from being spaced apart in the engaged storage configuration of the operably engaged first and second shuttle plates to abutting in the engaged loading configuration of the operably engaged first and second shuttle plates.

10. The shuttle of claim 9, wherein the flexure interface is linear.

11. The shuttle of claim 9, wherein the first shuttle plate includes a first haptic ramp and the second shuttle plate includes a second haptic ramp.

12. The shuttle of claim 9, further comprising a vial configured to releasably retain the shuttle in the engaged storage configuration.

13. The shuttle of claim 9, wherein the IOL chamber defines (i) a storage dimension for the optic of the IOL in the storage configuration and (ii) a loading dimension for the optic of the IOL in the loading configuration, wherein the loading dimension is smaller than the storage dimension.

14. The shuttle of claim 9, wherein the IOL chamber is axially bounded by a proximal port and a longitudinally spaced distal port, and includes an access port.

15. The shuttle of claim 9, wherein the IOL chamber and the flexure interface are intermediate the storage set of confronting surfaces and the loading set of confronting surfaces along a direction transverse to the longitudinal axis.

* * * * *